US010089444B2

(12) United States Patent
Weber

(10) Patent No.: US 10,089,444 B2
(45) Date of Patent: *Oct. 2, 2018

(54) IMAGE ACQUISITION FOR MEDICAL DOSE PREPARATION SYSTEM

(71) Applicant: Baxter Corporation Englewood, Englewood, CO (US)

(72) Inventor: Wesley J. Weber, Golden, CO (US)

(73) Assignee: Baxter Corporation Englewood, Englewood, CO (US)

(*) Notice: Subject to any disclaimer, the term of this patent is extended or adjusted under 35 U.S.C. 154(b) by 22 days.

This patent is subject to a terminal disclaimer.

(21) Appl. No.: 15/339,390

(22) Filed: Oct. 31, 2016

(65) Prior Publication Data

US 2017/0046502 A1 Feb. 16, 2017

Related U.S. Application Data

(63) Continuation of application No. 14/438,544, filed as application No. PCT/US2013/032497 on Mar. 15, 2013, now Pat. No. 9,489,489.

(Continued)

(51) Int. Cl.
*H04N 7/18* (2006.01)
*G06F 19/00* (2018.01)
(Continued)

(52) U.S. Cl.
CPC ........ *G06F 19/3456* (2013.01); *G06F 19/321* (2013.01); *G06Q 10/08* (2013.01);
(Continued)

(58) Field of Classification Search
None
See application file for complete search history.

(56) References Cited

U.S. PATENT DOCUMENTS 4,414,566 A  11/1983  Peyton et al.
4,653,010 A   3/1987  Figler et al.
(Continued)

FOREIGN PATENT DOCUMENTS

GB        994977 A    6/1965
JP      2000036032 A   2/2000
(Continued)

OTHER PUBLICATIONS

Phillips, Jon, Associate Director of Telemedicine, "Telepharmacy at Texas Tech," presented Apr. 30, 2003, published at http://www.ttuhsc.edu/telemedicine/publication.htm at least by Jun. 22, 2003.
(Continued)

*Primary Examiner* — Chikaodili E Anyikire
(74) *Attorney, Agent, or Firm* — K&L Gates LLP

(57) ABSTRACT

Use of improved image acquisition for a medical dose preparation system. The medical dose preparation system may include a work station for capturing medical dose preparation images (e.g., to document preparation of a mediation dose). The medical dose preparation image may be captured by a video data stream processor capable of performing an auto cropping technique on a video data stream received from an image device. Accordingly, memory resources may be more efficiently employed while maintaining high quality medical dose preparation images.

20 Claims, 12 Drawing Sheets

Related U.S. Application Data

(60) Provisional application No. 61/719,235, filed on Oct. 26, 2012.

(51) Int. Cl.
  *H04N 5/232* (2006.01)
  *G06Q 10/08* (2012.01)
  *G06Q 50/22* (2018.01)
  *G06Q 50/24* (2012.01)
  *G06T 7/136* (2017.01)
  *G06T 7/00* (2017.01)
  *G06T 7/11* (2017.01)

(52) U.S. Cl.
  CPC .............. *G06Q 50/22* (2013.01); *G06Q 50/24* (2013.01); *G06T 7/0012* (2013.01); *G06T 7/136* (2017.01); *H04N 5/23293* (2013.01); *H04N 7/183* (2013.01); *A61J 2205/40* (2013.01); *G06T 7/11* (2017.01); *G06T 2207/20132* (2013.01)

(56) References Cited

U.S. PATENT DOCUMENTS

| | | |
|---|---|---|
| D293,135 S | 12/1987 | Medema et al. |
| 5,431,201 A | 7/1995 | Torchia et al. |
| 5,509,318 A | 4/1996 | Gomes |
| 5,651,775 A | 7/1997 | Walker et al. |
| D385,646 S | 10/1997 | Chan |
| 5,713,485 A | 2/1998 | Liff et al. |
| 5,797,515 A | 8/1998 | Liff et al. |
| 5,818,528 A | 10/1998 | Roth et al. |
| 5,907,493 A | 5/1999 | Boyer et al. |
| D414,578 S | 9/1999 | Chen et al. |
| 6,068,156 A | 5/2000 | Liff et al. |
| 6,283,322 B1 | 9/2001 | Liff et al. |
| 6,330,491 B1 | 12/2001 | Lion |
| 6,438,451 B1 | 8/2002 | Lion |
| 6,471,089 B2 | 10/2002 | Liff et al. |
| 6,564,121 B1 | 5/2003 | Wallace et al. |
| 6,581,798 B2 | 6/2003 | Liff et al. |
| 6,610,973 B1 | 8/2003 | Davis, III |
| 6,711,460 B1 | 3/2004 | Reese |
| 6,735,497 B2 | 5/2004 | Wallace et al. |
| 6,776,304 B2 | 8/2004 | Liff et al. |
| 6,814,255 B2 | 11/2004 | Liff et al. |
| 6,877,530 B2 | 4/2005 | Osborne et al. |
| 6,915,823 B2 | 7/2005 | Osborne et al. |
| 6,981,644 B2 | 1/2006 | Cheong et al. |
| 6,991,002 B2 | 1/2006 | Osborne et al. |
| 7,006,893 B2 | 2/2006 | Hart et al. |
| 7,017,622 B2 | 3/2006 | Osborne et al. |
| 7,028,723 B1 | 4/2006 | Alouani et al. |
| 7,117,902 B2 | 10/2006 | Osborne |
| 7,151,982 B2 | 12/2006 | Liff et al. |
| 7,240,699 B2 | 7/2007 | Osborne et al. |
| 7,427,002 B2 | 9/2008 | Liff et al. |
| 7,499,581 B2* | 3/2009 | Tribble ................... B65B 3/003 250/577 |
| 7,561,312 B1 | 7/2009 | Proudfoot et al. |
| 7,610,115 B2 | 10/2009 | Rob et al. |
| 7,753,085 B2 | 7/2010 | Tribble et al. |
| 7,783,383 B2 | 8/2010 | Eliuk et al. |
| D624,225 S | 9/2010 | Federico et al. |
| 7,931,859 B2 | 4/2011 | Mlodzinski et al. |
| 7,991,507 B2 | 8/2011 | Liff et al. |
| 8,191,339 B2 | 6/2012 | Tribble et al. |
| 8,215,557 B1 | 7/2012 | Reno et al. |
| 8,220,503 B2* | 7/2012 | Tribble ................... B65B 3/003 141/104 |
| 8,225,824 B2 | 7/2012 | Eliuk et al. |
| D667,961 S | 9/2012 | Marmier |
| 8,267,129 B2 | 9/2012 | Doherty et al. |
| 8,271,138 B2 | 9/2012 | Eliuk et al. |
| 8,280,549 B2 | 10/2012 | Liff et al. |
| 8,374,887 B1 | 2/2013 | Alexander |
| 8,386,070 B2 | 2/2013 | Eliuk et al. |
| 8,554,579 B2 | 10/2013 | Tribble et al. |
| D693,480 S | 11/2013 | Spiess et al. |
| 8,678,047 B2 | 3/2014 | Tribble et al. |
| D715,958 S | 10/2014 | Bossart et al. |
| D738,152 S | 9/2015 | Grasselli et al. |
| D753,428 S | 4/2016 | Shao |
| 9,382,021 B2 | 7/2016 | Tribble et al. |
| 2002/0100762 A1 | 8/2002 | Liff et al. |
| 2003/0050731 A1 | 3/2003 | Rosenblum |
| 2003/0231803 A1 | 12/2003 | Huang |
| 2004/0172289 A1 | 9/2004 | Kozic et al. |
| 2004/0204954 A1 | 10/2004 | Lacko |
| 2005/0001033 A1 | 1/2005 | Cheong et al. |
| 2005/0080651 A1 | 4/2005 | Morrison et al. |
| 2007/0047980 A1 | 3/2007 | Limer et al. |
| 2007/0216998 A1 | 9/2007 | Sander |
| 2007/0239482 A1 | 10/2007 | Finn et al. |
| 2009/0285762 A1* | 11/2009 | Flower ............... A61K 49/0021 424/9.6 |
| 2009/0324032 A1 | 12/2009 | Chen |
| 2010/0017031 A1 | 1/2010 | Rob et al. |
| 2010/0091281 A1 | 4/2010 | Suzuki |
| 2010/0094653 A1* | 4/2010 | Tribble ................. G06F 19/326 705/3 |
| 2010/0128165 A1 | 5/2010 | Newcomb et al. |
| 2010/0241270 A1 | 9/2010 | Eliuk et al. |
| 2011/0208350 A1 | 8/2011 | Eliuk et al. |
| 2011/0267465 A1 | 11/2011 | Alexander et al. |
| 2012/0097290 A1 | 4/2012 | Mikhaeil |
| 2012/0200596 A1 | 8/2012 | Gotou et al. |
| 2013/0079581 A1* | 3/2013 | Agamaite ............ A61N 5/1027 600/4 |
| 2013/0197445 A1* | 8/2013 | Schabbach ......... A61B 5/14532 604/189 |
| 2013/0279774 A1 | 10/2013 | Helgason et al. |
| 2013/0314535 A1 | 11/2013 | Yuyama et al. |
| 2013/0342676 A1* | 12/2013 | Amano .................... H04N 7/18 348/86 |

FOREIGN PATENT DOCUMENTS

| | | |
|---|---|---|
| JP | 2004340770 A | 2/2004 |
| JP | 2005252710 A | 9/2005 |
| JP | 2006033291 A | 2/2006 |
| JP | 2006334062 A | 12/2006 |
| JP | 4276654 B2 | 6/2007 |
| JP | 2007198934 A | 8/2007 |
| JP | 2008139201 A | 6/2008 |
| JP | 2009265827 A | 11/2009 |
| JP | 2010056619 A | 3/2010 |
| JP | 2010508571 A | 3/2010 |
| JP | 2010170504 A | 8/2010 |
| JP | 2011151430 A | 8/2011 |
| JP | 2012078265 A | 4/2012 |
| KR | 1020110115927 A | 10/2011 |
| WO | 2012056317 A2 | 5/2012 |

OTHER PUBLICATIONS

Peterson, Charles D. and Anderson, Jr., Howard C.; "The North Dakota Telepharmacy Project: Restoring and Retaining Pharmacy Services in Rural Communities," Jan./Feb. 2004.
Texas Administrative Code, Title 22, Part 15, Ch 291, Rules 20, 36, and 71-74. Feb. 10, 2004.
Cato Reference Manual, Support for Trial Version (Abridged), Vienna, Jun. 2004.
Seifert et al., "The Training of a Telepharmacist: Addressing the Needs of Rural West Texas," American Journal of Pharmaceutical Education 2004, 68 (3) Article 60, Jul. 16, 2004.
GE Healthcare, "ImageQuant TL 7.0 Image Analysis Software" User Manual, May 2007, http://nba.uth.tmc.edu/Assets/pdf/other/typhoon_supporting_files/IQTL_UserManual.pdf, Uppsala, Sweden.

(56) References Cited

OTHER PUBLICATIONS

Forhealth Technologies, Inc., "IntelliFlowRx The World's First Fully Integrated Workflow Manager for I.V. Rooms", Brochure, United States, May 2008.
Baxa Corporation, "DoseEdge the Leading Edge in Dose Management", Brochure, published copyright date 2010.
Parsons, et al., "Digital Media—Can I Change a Graphic's File Size?", New Perspectives on Computer Concepts—Course Technology, 2011, Cengage Learning, Boston, MA.
Baxa Corporation, "Product Catalog 2010-2011", published at least by Sep. 15, 2012, https://web.archive.org/web/20120915210739/http://ww.baxa.com/resources/docs/BaxaCatalog.pdf.
Japanese Office Action dated Nov. 14, 2017 (and English language translation) in corresponding Japanese Application No. 2016-111361.

\* cited by examiner

IMAGE ACQUISITION FOR MEDICAL DOSE PREPARATION SYSTEM

RELATED APPLICATIONS

This application is a continuation of U.S. patent application Ser. No. 14/438,544, filed Apr. 24, 2015, entitled "IMPROVED IMAGE ACQUISITION FOR MEDICAL DOSE PREPARATION SYSTEM," which is a U.S. National Stage of International Patent Application No. PCT/US2013/032497, filed Mar. 15, 2013, entitled, "IMPROVED IMAGE ACQUISITION FOR MEDICAL DOSE PREPARATION SYSTEM," which claims benefit of priority to U.S. Provisional Patent Application No. 61/719,235 filed Oct. 26, 2012, entitled "IMPROVED IMAGE ACQUISITION FOR MEDICAL DOSE PREPARATION SYSTEM," all of which foregoing patent applications are incorporated herein by reference in their entirety.

BACKGROUND OF THE INVENTION

Many care providers have a pharmacy that prepares medical doses for administration to patients that are treated by the care provider. In this regard, the pharmacies may employ a formulary to prepare medications in order to fulfill medical dose orders that are ordered by care provider personnel (e.g., physicians) for administration to patients. Some medical doses to be prepared may include compounded sterile products (CSPs) that may be prepared in a specially constructed and controlled environment (e.g., an "IV Room") in the pharmacy. The process of preparing medical doses may be carried out in accordance with local care provider policy, governmental regulations, industry organizations (e.g., Chapter <797> of the United States Pharmacopoeia), or other applicable policies. For example, the preparation of medications may generally occur in a laminar airflow hood, isolator, or biological safety cabinet, by an operator (typically a pharmacy technician) who is tasked with preparing the medical doses. Once the medical doses are prepared, the medical doses may be required to be verified by a pharmacist prior to being dispensed from the pharmacy for administration to a patient.

In traditional pharmacy management techniques, medical dose orders may be provided to a printer that prints labels indicative of the medical dose order that are to be applied to finished doses once the doses are prepared. A pharmacy technician may be required to retrieve labels from a label printer and use those labels as work order travelers in the process of preparing each dose. Once the dose is prepared, the technician may apply a label to the dose. The completed, labeled dose may be set aside for a pharmacist to check along with, for example, source ingredients, medication receptacles used in the course of preparing the dose, and/or other material. In this regard, in order to check a dose, the pharmacist may be required to enter the clean room in which the doses are prepared and physically observe the materials associated with the dose order. As such, the checking of prepared doses may require the pharmacist to dress in protective clothing or equipment, which takes time and resources.

Furthermore, the only prompt a pharmacy may receive to prepare a medical dose order is the printing of the label. In this regard, if a label becomes lost or damaged, a dose may not be prepared. Additionally, prioritizing work also becomes difficult because the label stack at the label printer may be the only evidence of what doses have been ordered, prepared, and/or dispensed. As such, relying on physical labels alone to track doses may result in unprepared, lost, or duplicate doses. In some cases, pharmacies may produce duplicate labels as a matter of course such that the pharmacy must review each label against the other, already received labels, to determine if a label represents a new dose order that needs to be prepared. This practice may lead to increased administrative overhead in the pharmacy that add operational costs and reduce pharmacy efficiency.

Furthermore, while instructions for preparation of a drug may be recorded in official FDA-approved literature for the drug, pharmacy technicians may not reliably consult the literature when preparing doses. Rather, pharmacy technicians may memorize the steps needed for the most common drugs, and then generalize those steps to other drugs to be prepared without verifying the protocols associated with a particular drug. In this regard, if the dose order includes special instructions that a pharmacy technician does not recognize, references regarding the proper techniques may not be present or may not be consulted. Accordingly, dose orders including special instructions often must be prepared by more experienced technicians or at the direction of more experienced technicians. In either regard, the protocol used to prepare the dose may not conform to the FDA-approved literature for the drug being prepared.

Further still, in traditional pharmacy management techniques, the pharmacy technician may be responsible for creating records that are maintained in relation to doses that have been prepared and products from the formulary that were employed to make the dose. For example, a pharmacy technician may be tasked with transcribing information such as lot numbers, expiration dates, serial numbers, or the like. The manual creation of records requires labor intensive practices that may result in pharmacy inefficiencies, introduces the potential for errors in the records, and may result in virtually unsearchable paper records.

SUMMARY OF THE INVENTION

In this regard, the present disclosure relates to embodiments of a medical dose preparation management system. The medical dose preparation management system may be capable of receiving dose orders, creating digital dose orders from the received dose orders, and managing the digital dose orders. For example, the medical dose preparation management system may be operable to create and store information related to the preparation of medical doses. Such information may be used to verify a medical dose order by a pharmacist, track a medical dose order in a pharmacy or care provider, be retained in connection with the digital dose order record for auditing, compliance, or quality assurance purposes, or otherwise be utilized in the management of the dose order before or after administration to a patient. In other words, the medical dose preparation management system may provide, in an automatic manner, an improved system that allows tracking a medical dose order in a pharmacy or care provider. The medical dose preparation management system may provide, in an automatic manner that the medical dose be retained in connection with the digital dose order record for auditing, compliance, or quality assurance purposes, or otherwise be utilized in the management of the dose order before or after administration to a patient. Hence, the medical dose preparation management system provides an improved man machine interaction, among others meeting the high level of compliance requirements in drug manufacturing and distribution with little or without any interference of a human personnel necessary. One example of information that may be created and stored in connection with a medical dose order is one or more medical dose preparation images. For example, a work station at which a dose order is prepared may include an imaging device (e.g., a digital camera) capable of capturing images related to the preparation of the medical dose. In an embodiment, the medical dose preparation images may include medication receptacles used in the preparation of the dose including, for example, a source receptacle, a transference receptacle, and/or an administration receptacle. Accordingly, the medical dose preparation images may be used to document or evidence the preparation of a medical dose order. Thus, the system provides an improved man machine interaction since less or even no interaction by a human person is necessary and still allows for accurate and trustworthy documentation.

Given the potential for capturing and storing a large number of medical dose preparation images, it may be advantageous to reduce the size in memory of medical dose preparation images. However, as such images may be used in a variety of contexts (e.g., including during verification of dose orders by a pharmacist), image quality is generally of great concern such that resolution is preferably not reduced when storing medical dose preparation images. In this regard, reduction in the physical size of an image (i.e., cropping the image to remove uninformative or useless portions of the image) may be used to effectively reduce the size of a medical dose preparation image in memory without reducing the resolution of the image.

However, manually cropping each medical dose preparation image may be burdensome and increase the cost and time required to prepare doses. In this regard, an apparatus described herein may employ an auto cropping operation to automatically reduce the size in memory of medical dose preparation images. For example, a region of interest in an image may be determined. The region of interest in an image may be captured as a medical dose preparation image that eliminates at least a portion of image data not within the region of interest.

Thus, the amount of image data stored in memory may be reduced without a reduction in resolution of the corresponding image and/or the resolution of a captured image may be increased while maintaining or reducing the amount of corresponding image data stored in memory. That is, for a given image resolution, the amount of corresponding image data may be reduced by reducing the size of the image. Thus, with little hardware resources, e.g., little memory capacity, a large amount of data can be stored. Moreover, with little hardware resources, e.g., little processing power, image data can be processed.

Additionally or alternatively, for a given amount of image data, a higher resolution image may be stored if the corresponding image data is only that of a cropped portion of the image. Accordingly, if the amount of image data is reduced, the computational overhead required to process, store, or otherwise take action with respect to the image may be reduced such that work flows at the work station may occur more quickly. Additionally or alternatively, if the resolution of an image is increased, a review of the image may be improved by allowing for capture of finer details (e.g., to allow for magnification of the image during a review by a pharmacist or the like).

In this regard, a first aspect described herein includes an apparatus for processing medical dose preparation image data in a system for medical dose preparation management. The system includes an imaging device (e.g., a digital camera) having an imaging field encompassing a medical dose preparation staging region. The imaging device is operable to output digital image data (e.g., corresponding to still digital images, a digital video data stream, and/or other forms of digital image data) of the imaging field including the medical dose preparation staging region. The system also includes a processor in operative communication with the imaging device to receive the digital image data of the imaging field. The system allows for automation of documenting medical dose order preparation and/or delivery. In particular the system may allow for such automation at a very high speed and/or increased image resolution which would otherwise not be possible by a human person. In other words, the system advantageously combines digital image processing with medical dose order preparation and/or drug delivery that would otherwise not have been done, since, according to this application, data processing may be carried at a high speed and/or with increased image resolution.

The system of the first aspect may include a display that is in operative communication with the processor to receive the digital image data of the imaging field and display a corresponding image that is perceivable by a user. The processor is operable to process the digital image data to identify at least one region of interest within the imaging field corresponding to at least one medication receptacle disposed in the medical dose preparation staging region. As such, in the event a display is utilized as described above, the region of interest may be visually differentiated on the display by the processor in a manner perceivable by the user. Hence, by the system, without the need of physically controlling the imaging device or accessing one or more medication receptacles at the medical dose preparation staging region, by a human person, it is possible to allow for the high level of documentation desired in medical dose preparation and/or delivering. In other words, the system allows relieving the human person from and/or assisting the user in the task of manual steps to obtain detailed documentation (e.g., detailed image data). Even more, since the documentation is machine aided or even completely carried out by the machine, namely the system described in this application, the documentation is more reliably or trustworthy as compared to the documentation by a human person. It may even only be possible to assure such documentation since the system strictly follows machine rules without deviation such as are possible for a human person.

The system of the first aspect may also include a user control device that is in operative communication with the processor to initiate the capture of a medical dose preparation image data from the digital image data. Other embodiments may include other mechanisms for initiating the capture of a medical dose preparation image. In any regard, the medical dose preparation image data may include image data corresponding to at least a portion of the region of interest and may exclude at least a portion of the imaging field (e.g., corresponding to a portion of the image data outside the region of interest). The system may also include a memory in operative communication with the processor to receive and store the medical dose preparation image data. The user control device provides for improved man machine interaction due to, e.g., in connection with the processor automatically processing the image.

A number of feature refinements and additional features are applicable to the first aspect. These feature refinements and additional features may be used individually or in any combination. As such, each of the following features that will be discussed may be, but are not required to be, used with any other feature or combination of features of the first aspect.

In an embodiment, the processor may be operable to analyze the digital image data to identify the region of interest. For example, the processor may be operable to analyze a predetermined subset of the digital image data (e.g., a subset of the pixels of the digital image data) to identify the region of interest. The subset may correspond to a predetermined portion of the digital image data such that the analysis of the image data may be executed on a portion, but not the entirety of the digital image data.

In an application, the analysis may include comparing the digital image data to a background image of the medical dose preparation staging region. In this regard, the background image may not include any medication receptacle in the medical dose preparation staging region. That is, the background image may represent the appearance of the medical dose preparation staging region in the absence of any object (e.g., a medication receptacle or the like). Accordingly, the predetermined subset of the digital image data may be compared to a corresponding subset of the background image. For example, corresponding ones of the subset of pixels in the digital image data and the background image may be compared.

In an application, the plurality of pixels may extend across substantially the entire digital image data in at least a first direction (e.g., a width of the image data). Additionally, the plurality of pixels may extend across substantially all of the digital image data in a second direction perpendicular to the first direction (e.g., a height of the image data). As such, the plurality of pixels corresponding to the predetermined subset of the image data may form a grid over the digital image data. The grid may comprise grid lines that are spaced in relation to a known size of medication receptacles. For instance, the grid lines may be spaced such that at least two grid lines cross the medical receptacle in at least two dimensions (e.g., corresponding to both a width and a length of the receptacle) even for the smallest known medication receptacle to be imaged.

In an embodiment, the region of interest may be defined by a bounding area defined by a plurality of edges. Each of the plurality of edges may be disposed at an identified location of the predetermined subset of the digital image data (e.g., along at least a portion of a grid line) at least partially based on a threshold difference between the digital image data and the background image at the identified location. In one example, the processor may be operable to calculate intensity data for each pixel of the predetermined subset of the digital image data and for each pixel of the corresponding predetermined subset of the background image. The intensity data may be filtered (e.g., high pass and/or low pass filtering). The threshold difference may correspond to a predetermined difference in intensity data between the predetermined subset of the digital image data and the background image.

In various embodiments, the digital image data may include discrepancies relative to the background image that, rather than being attributable to the presence of a medication receptacle, are solely attributable to slight variations in positions of the background image relative to the background of the digital image data, lighting variations, or other minor discrepancies. In this regard, each pixel of the predetermined subset may be compared to a plurality of adjacent corresponding pixels from the background image. In this regard, insignificant variations related to the discrepancies disclosed above may be disregarded in the analysis.

In an application, the identified location resulting from the comparison of intensity data between the digital image data and the background image may correspond to one of a minimum and/or maximum threshold difference along the grid lines in a first direction and/or in a second direction. That is, two threshold differences may be identified in either or both of the first and second direction corresponding to the extents of the medication receptacle in the width and/or height dimension. In still another application, the identified location may be selected to correspond to the next most remote grid line of the grid exterior to the threshold difference in the first direction and in the second direction along the grid line. As such, if a portion of the medication receptacle extends beyond a grid line along which a threshold difference is identified, the full portion of the receptacle may still be contained in the region of interest if the identified location is selected as the next remote grid line. Summarizing the above, the system provides an improved man machine interaction, e.g., by relieving the user from and/or assisting the user in the manual and/or mental task to control the imaging device or manipulate one or more medication receptacles.

A second aspect described herein includes a method for processing and capturing medical dose preparation image data. The method includes encompassing a medical dose preparation staging region in an imaging field of an imaging device. The method further includes obtaining digital image data of the imaging field. The method also includes identifying, at a processor in operative communication with the imaging device, a region within the imaging field corresponding to at least one medication receptacle disposed in the medical dose preparation staging region. The method may also include displaying the digital image data on a display. The region of interest may be visibly distinguished by the processor on the display in a manner that is perceivable by a user.

The method of the second aspect may also include receiving an input from a user control device to initiate capture of medical dose preparation image data from the digital image data. The medical dose preparation image data includes image data corresponding to at least a portion of the region. The method further includes storing the medical dose preparation image data in a memory. In various method embodiments, the method may employ a system comprising any of the system features described herein.

According to yet another aspect, a computer program product is provided that can be stored on a computer readable medium and/or can be implemented as computer processable data stream, wherein the computer program product comprises computer processable instructions, which instructions when read in the memory of a computer and executed by the computer cause the computer to carry out the method(s) as described in general above, and in more specific examples below.

A number of feature refinements and additional features are applicable to the second aspect. These feature refinements and additional features may be used individually or in any combination. As such, each of the following features that will be discussed may be, but are not required to be, used with any other feature or combination of features of the second aspect.

For example, the speed at which the identifying operation occurs may be important to the method of the second aspect. As may be appreciated, the volume of dose orders prepared in a pharmacy or the like may be relatively large. As such, efficient preparation of the medical dose order may be of great importance. In this regard, it may be desirable to have any auto cropping operation occur relatively quickly so as to prevent preparation delays when preparing the medical dose order.

Accordingly, in an embodiment, the digital image data may comprise a video stream data. In this embodiment, the identifying may occur more rapidly than a refresh rate of the video data stream. As such, each successive frame of the video data stream may undergo the auto cropping operation without slowing the speed at which the video data stream is captured or displayed.

Numerous additional features and advantages of the present invention will become apparent to those skilled in the art upon consideration of the embodiment descriptions provided hereinbelow.

DETAILED DESCRIPTION

Figure 1:
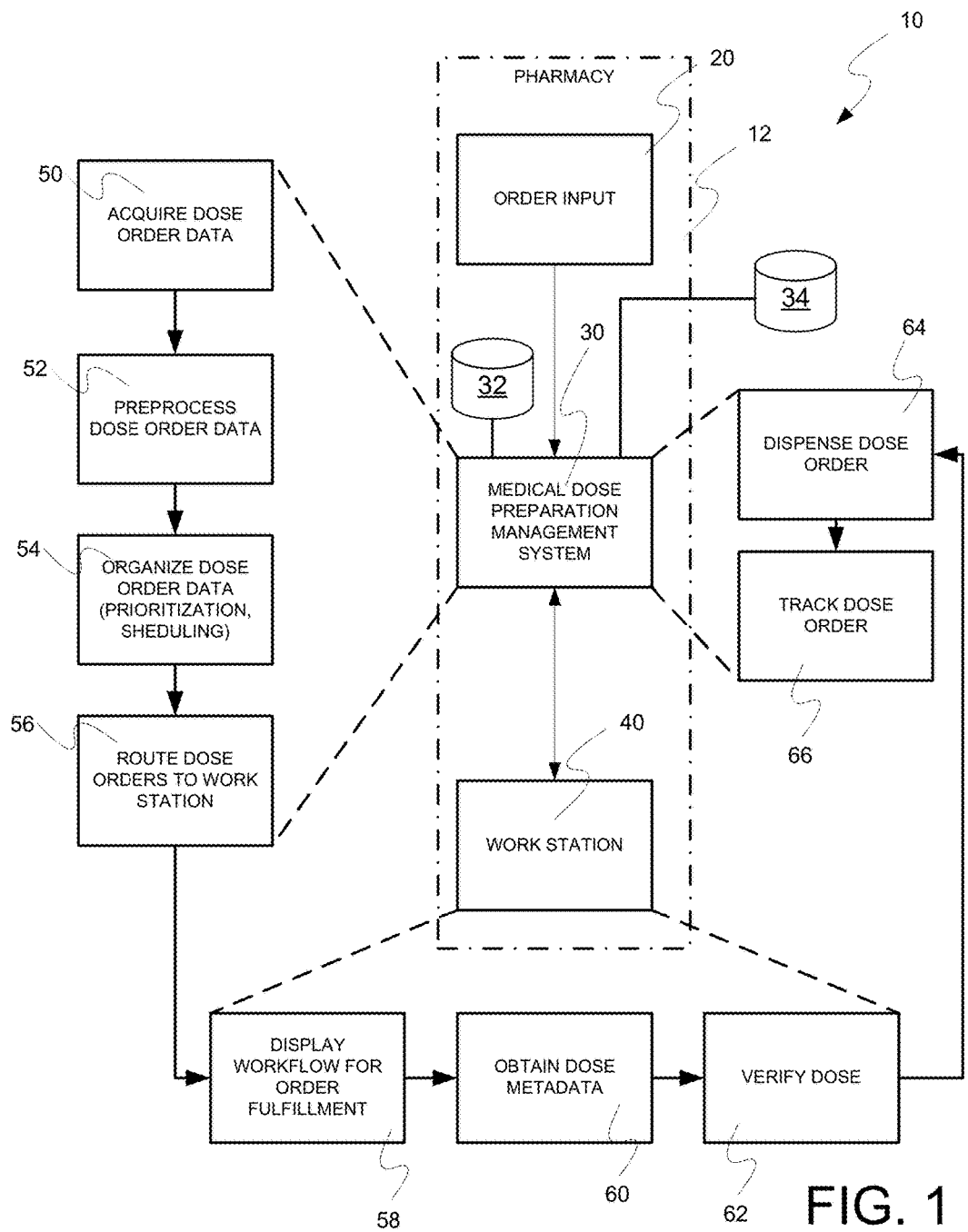
FIG. 1 is a schematic and flow chart depicting an embodiment of a medical dose preparation management system and an embodiment of the operation thereof.

While the invention is susceptible to various modifications and alternative forms, specific embodiments thereof have been shown by way of example in the drawings and are herein described in detail. It should be understood, however, that it is not intended to limit the invention to the particular form disclosed, but rather, the invention is to cover all modifications, equivalents, and alternatives falling within the scope of the invention as defined by the claims.

FIG. 1 shows an embodiment of a system 10 that may be used at a care provider pharmacy 12 to assist in the preparation and/or management of medical doses. The system 10 may include a dose order input 20 to receive medical dose orders. The dose order input 20 may be utilized by care provider personnel (e.g., physicians, nurses, etc.) to order medical doses.

The medical dose orders received at the dose order input 20 may be specific to patients or may be orders that are not associated with a patient at the time of ordering. In this regard, the medical dose order may correspond to a contained medication unit that may comprise one of the following:
- a patient specific unit comprising a medication unit designated for administration to a specific patient;
- a non-patient specific unit comprising a medication unit to be subsequently designated for administration to a specific patient; or,
- a medication component source unit to be used in the preparation of a patient specific unit or a non-patient specific unit (e.g., that will be designated for administration to a specific patient after preparation).

Examples of contained medication units that may correspond to medication dose orders include:
- compounded sterile products;
- injectable medications;
- chemotherapy preparations; or
- nutritional supplements requiring administration by a patient care provider (e.g., sterile injectable nutritional supplements).

In the latter regard, nutritional supplements may include total parenteral nutrition (TPN) or components of TPN. Furthermore, nutritional supplements may include partial nutritional supplements. The nutritional supplements may include a pre-mix bag, base and additive components separately or in combination, or other forms of nutritional supplements or components thereof. The nutritional supplements may be for administration via intravenous injections, in an edible form, or for use with a feeding tube or the like.

In any regard, the medical dose may include one or more portions of information that may be used to assist in preparation of the mediation dose, may be associated with the administration of the dose order to a patient, or may otherwise relate to the dose order. For example, the dose order may include information corresponding to:
- a medication identity;
- a medication amount;
- a medication concentration;
- information associated with a patient to whom the medication unit associated with the medication dose order is to be administered;
- scheduling information (e.g., an administration time) for the medication unit associated with medication dose order; or
- other appropriate information regarding the medication unit associated with the medication dose order.

In any regard, the medical dose orders may be communicated to a medical dose preparation management system 30. The medical dose preparation management system 30 may be operable to acquire 50 dose order data from the dose order information received from the order processor 20. The medical dose preparation management system 30 may also preprocess 52 dose order data. The preprocessing 52 may include, for example, generating a digital dose order record that is maintained by the medical dose preparation management system 30. The digital dose order record may be automatically populated with data that may be obtained from the order such as, for example, any of the information described above in connection with the medical dose order. In this regard, information may be parsed, scraped, or otherwise obtained from the medication dose order received at the order input 20. Specifically, in an embodiment, the medical dose preparation management system 30 may be operable to scrape data addressed to a human readable output (e.g., a printer) from the order input 20 to populate the medical dose order record with data corresponding to the medical dose order.

In an embodiment, the medical dose preparation management system 30 may be in operative communication with a medication dose order database 32. In this regard, the medication dose order database 32 may be located at the care provider facility (i.e., be on-site relative to the care provider hospital 12). The medical dose preparation management system 30 may additionally or alternatively be operable to communicate with a remote medication dose order database 34. In this regard, the medical dose preparation management system 30 may communicate with the remote medication dose order database 34 via a network or the like. In either regard, the medication dose order database 32 or 34 may be operable to store medication dose order records in the medication dose order database 32 and/or 34. In addition, the medication dose order database 32 or 34 may store dose order metadata in corresponding relation to respective ones of the stored medication dose orders. The medication dose order database 32 or 34 may store active dose orders (e.g., corresponding to dose orders that have been generated but not yet administered to the patient) or archived dose orders (e.g., corresponding to dose orders that have been administered to a patient). Redundant data may be stored at the on-site medical dose order database 32 and the off-site medical dose order database 34. For example, the off-site medical dose order database 34 may be a backup version of the on-site medical dose order database 32.

In any regard, medical dose order metadata may be stored in corresponding relation to a medication dose order. The medical dose order metadata may include, for example, the following types of data:

medication source data indicative of at least one of:
- a manufacturer of a component of the contained medication unit corresponding to the medication dose order,
- a lot number of a component of the contained medication unit corresponding to the medication dose order,
- an expiration date of a component of the contained medication unit corresponding to the medication dose order,
- a serial number of a component of the contained medication unit corresponding to the medication dose order, or
- a drug code indicative of the identity of a component of the contained medication unit corresponding to the medication dose order;

chain of custody data indicative of at least one of:
- a listing of entities in possession of a component of the contained medication unit corresponding to the medication dose order or the contained medication unit corresponding to the medication dose order,
- a listing of users that have taken an action with respect to the contained medication unit corresponding to the medication dose order, wherein the listing of users is correlated to specific actions taken by each user, or
- tracking information corresponding to physical movement of a component of the contained medication unit corresponding to the medication dose order or the contained medication unit corresponding to the medication dose order;

fulfillment data indicative of at least one of:
- image data corresponding with a component of the contained medication unit corresponding to the medication dose order or the contained medication unit corresponding to the medication dose order,
- scanned data obtained from a component of the contained medication unit corresponding to the medication dose order,
- analytic data regarding a component of the contained medication unit corresponding to the medication dose order or the contained medication unit corresponding to the medication dose order,
- pharmacist review data corresponding with at least one pharmacist review of a component of the contained medication unit corresponding to the medication dose order or the contained medication unit corresponding to the medication dose order,
- compliance data corresponding with best practices associated with a component of the contained medication unit corresponding to the medication dose order or the contained medication unit corresponding to the medication dose order,
- sterility assessment data corresponding to a component of the contained medication unit corresponding to the medication dose order or the contained medication unit corresponding to the medication dose order,
- a listing of actions corresponding to a component of the contained medication unit corresponding to the medication dose order or the contained medication unit corresponding to the medication dose order,
- time stamp data corresponding to actions corresponding to a component of the contained medication unit corresponding to the medication dose order or the contained medication unit corresponding to the medication dose order,
- a listing of life cycle events taken with respect a component of the contained medication unit corresponding to the medication dose order or the contained medication unit corresponding to the medication dose order, or
- weight data corresponding to a measured and/or anticipated weight of a component of the contained medication unit corresponding to the medication dose order or the contained medication unit corresponding to the medication dose order; or environmental data indicative of at least one of:
- a temperature to which a component of the contained medication unit corresponding to the medication dose order or the contained medication unit corresponding to the medication dose order has been exposed,
- a temperature to which and corresponding time period for which a component of the contained medication unit corresponding to the medication dose order or the contained medication unit corresponding to the medication dose order has been exposed,
- whether a component of the contained medication unit corresponding to the medication dose order or the contained medication unit corresponding to the medication dose order is refrigerated,
- whether a component of the contained medication unit corresponding to the medication dose order or the contained medication unit corresponding to the medication dose order is frozen,
- a temperature profile experienced by a component of the contained medication unit corresponding to the medication dose order or the contained medication unit corresponding to the medication dose order, or
- accelerometer data corresponding to forces experienced by a component of the contained medication unit corresponding to the medication dose order or the contained medication unit corresponding to the medication dose order.

As may be appreciated from the foregoing description of the medical dose order metadata, a medical dose order may inherit metadata from components used in the preparation of the medical dose order. In a simple example, a medical dose order may include a first component (e.g., a drug) to be mixed with a second component (e.g., a diluent). The first component may have one or more portions of metadata as described above that are associated with the first component. Additionally, the second component may have one or more portions of metadata as described above that are associated with the second component. Thus, a medical dose order that is prepared using the first component and the second component may inherit the metadata from each of the first component and second component. In this regard, a plurality of generations of metadata may be compiled and attributed for a given medical dose order. In an embodiment, metadata for any and all components used to prepare the dose order may be compiled and attributed for a given medical dose order. As such, metadata information for the medical dose order may include metadata originating with source components provided by a manufacturer of the components of a dose order.

The medical dose preparation management system 30 may also be operative to organize 54 dose orders. The organization 54 may include prioritization, scheduling, or other tasks associated with the organization or management of dose orders. The medical dose preparation management system 30 may also be operative to route 56 dose orders to an appropriate work station 40 for use in fulfillment of the dose order. In this regard, a plurality of work stations 40 may be provided in communication with the medical dose preparation management system 30. Different ones of the plurality of work stations 40 may each be suited for different operations related to medical dose order management. As such, depending on the nature of a medical dose, a particular type of work station 40 may be used to prepare the dose. The work station 40 may be on-site relative to the care provider hospital 12 as depicted in FIG. 1 or may be off-site. In this regard, the routing 56 may include communications over a network to a remote work station 40. Furthermore, the system 10 may include a combination of on-site work stations 40 as well as off-site work stations 40 to which dose orders may be routed 56.

In any regard, the medical dose preparation management system 30 may be in operative communication with one or more work stations 40. The routing 56 of dose orders may be at least partially based on one or more factors related to the dose order or the preparation of the dose order. For example, as stated above, the nature of the contained medication unit corresponding to the dose order (e.g., whether a dose order is a chemotherapy dose order, a parenteral dose order, or other specialized dose order) may factor into a determination regarding the routing 56 of the dose order. Additionally or alternatively, the capabilities of the various work stations 40 in relation to the manner in which the dose order is to be prepared may be considered. For example, some orders may require different levels of containment, hooding, or other precautions that may or may not be provided at each work station 40. In an embodiment, other parameters such as technician schedules, work station schedules, work station location, medication dose order scheduling information, or other information may be used alone or in combination to route 56 dose orders to a particular work station 40.

At the work station 40, a work flow corresponding to the preparation of the medical dose order may be displayed 58. In this regard, a work flow that is specific to the medical dose order currently being prepared at the work station 40 may be presented to a technician at the work station 40 to assist or provide guidance to the technician preparing the dose order. Accordingly, the technician may follow a sequence of steps to prepare the medical dose based on the work flow displayed 58 that relates to the dose order.

During and/or after the preparation of the dose order, the work station 40 may be used to assist in obtaining 60 dose order metadata related to the medical dose order. For example, the work station 40 may allow for recording of documentation regarding the preparation of the medical dose such as, for example, acquiring barcode scans of products, capturing medical dose preparation images of medical dose order receptacles during or after use in the preparation of the dose, or obtaining other information related to the preparation of the dose. In an embodiment, one or more of the types of data described above in relation to the medication dose metadata may be acquired in connection with the preparation of the medical dose order at the work station 40.

At least a portion of the dose metadata obtained 60 regarding the medication dose may be stored for viewing by appropriate personnel (e.g., a pharmacist). In this regard, the dose metadata may be utilized to verify 62 the prepared dose prior to the dose being dispensed from the pharmacy 12. In an embodiment, the metadata collected at the work station 40 may be made available to a pharmacist via a network. In this regard, a pharmacist tasked with verifying 62 a dose order may access the information and/or data remotely (e.g., in a location in the hospital but outside the IV room or even entirely remove from hospital premises via the network). The ability to remotely access the metadata may allow the pharmacist to avoid having to enter the IV room to verify 62 a dose order (i.e., thus avoid the potentially burdensome gowning procedures commonly associated with entering the controlled environment of an IV room). The verifying 62 may include inspection of medical dose preparation images, obtained information, or other data regarding the medical dose order by the pharmacist. For example, the pharmacist may verify the correct medication was prepared in the correct manner and/or in the correct amounts based on metadata gathered and stored during the preparation of the medical dose order. If the medication dose order is incorrect in any regard, the pharmacist may request the medication dose order be reworked or restarted.

Once the dose order has been prepared and verified 62, the medical dose preparation management system 30 may dispense 64 the dose order. When dispensing 64 the dose order, the dose order may be dispatched from the pharmacy 12 for administration to a patient by the care provider. For example, the dose may be administered at the care provider hospital 12 or an offsite location under the direction or supervision of the care provider.

The medical dose preparation management system 30 may also facilitate tracking 66 of the dose order to administration to the patient. The pharmacy work flow manager 30 may also retain records associated with each dose that may be stored or archived. For example, the records may be stored digitally in electronically indexed and searchable form. The records may include at least a portion and preferably all metadata regarding each dose.

Figure 2:
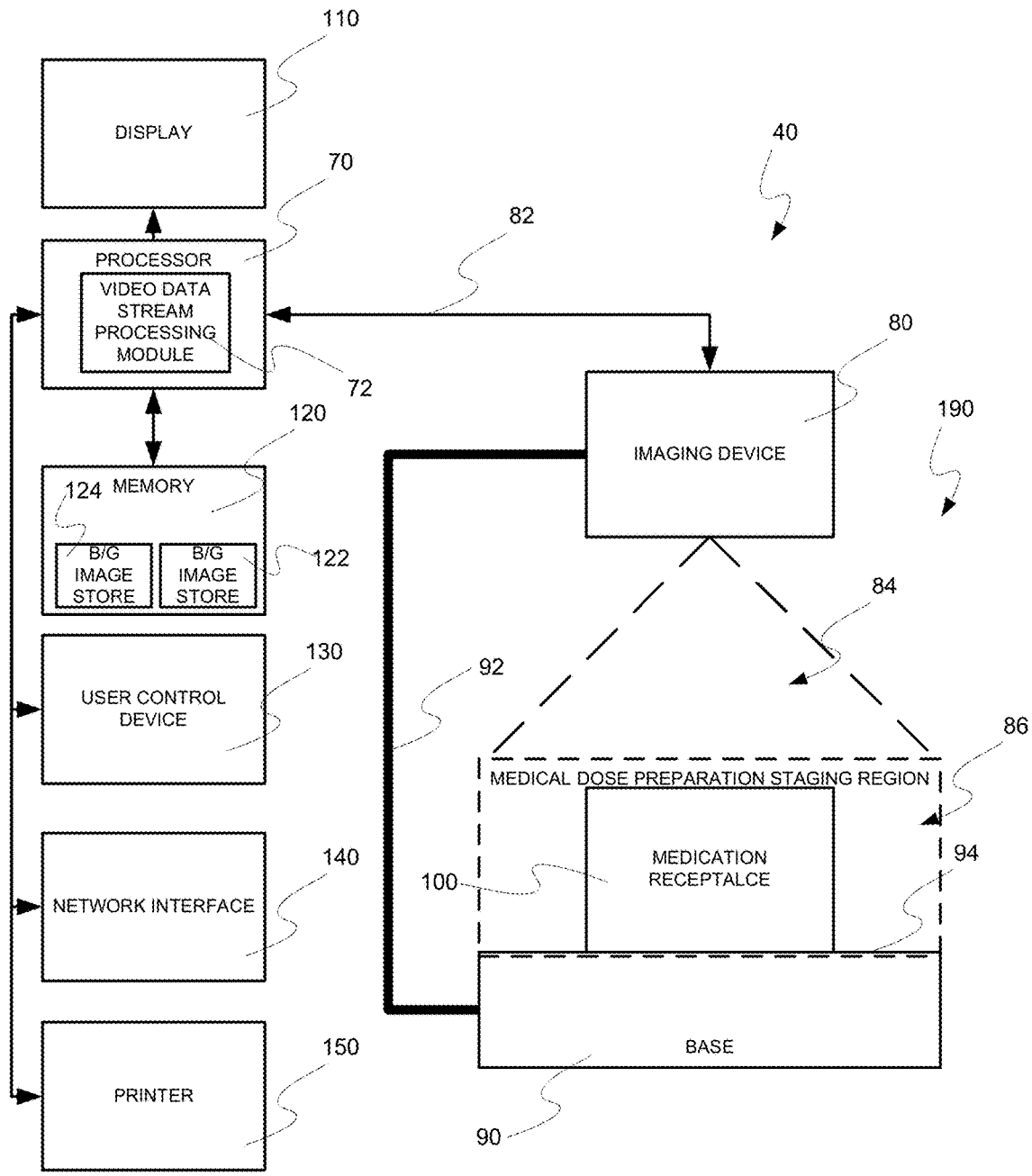
FIG. 2 is a schematic view of an embodiment of a work station for use in a medical dose preparation management system.

With further reference to FIG. 2, a schematic view depicting an embodiment of a work station 40 is shown. The work station 40 may include a processor 70 in operative communication with an imaging device 80. The imaging device 80 may be a digital camera operable to output digital image data. The digital image data may comprise still images and/or digital video. In this regard, the imaging device 80 may output a video data stream 82 that is received by the processor 70. In this regard, the processor 70 may include a video data stream processing module 72 for processing the video data stream 82 received at the processor 70 from imaging device 80. While the various components shown in FIG. 2 are shown in direct communication, the various components may also be in operative communication by way of a network interface or the like.

The imaging device 80 may include an imaging field 84. The imaging field 84 may encompass a medical dose preparation staging region 86. The imaging device 80 may be supportably mounted to a base 90. For example, a support 92 may extend from the base 90 to the imaging device 80 to support imaging device 80 relative to the base 80. In this regard, in an embodiment the medical dose preparation staging region 86 may include a support surface 94 of the base 90. The medical dose preparation staging region 86 may also include a volume above the surface 94 (e.g., extending from the surface in a direction normal to the surface and/or toward the imaging device 80). In any regard, the imaging field 84 of the imaging device 80 may encompass the medical dose preparation staging region 86 that may supportably receive a medication receptacle 100. In turn, the imaging device 80, support 92, and base 90 may collectively define a camera stand 190. As such, the camera stand 190 may be used at a work station 40 to support the imaging device 80 relative to the base 90 to obtain medical dose preparation image and/or other metadata during the preparation of the medical dose order.

The medication receptacle 100 supportable by the base 90 in the medical dose preparation staging region 86 may include any material, container, apparatus, or other object that is used in the preparation of a dose. For example, the medication receptacle 100 may be or include a source receptacle, a transference receptacle, or an administration receptacle. A source receptacle may store a medication product as stored in the pharmacy prior to compounding or dose preparation. In this regard, the source receptacle may be a receptacle as packaged by and received from a drug manufacturer. As such, the source receptacle may include information thereon relating to the medication. For example, the product name, concentration, amount, lot information, expiration information, a serial number, other manufacturing information or other information may be associated with the medication and/or may appear on the source receptacle. The medical dose preparation management system 30 may be operable to store metadata regarding the source receptacle including any of the foregoing portions of data that may appear on the source receptacle. In this regard, the source receptacle may be identifiable by the work station 40 (e.g., via the use of a machine readable indicium such as a bar code or the like).

Furthermore, the medical dose preparation management system 30 may be operable to attribute metadata from the source receptacle to the dose order in which the source receptacle is used as described above. The source receptacle metadata may even be attributed to or appended to the metadata for the medical dose order when the source receptacle comprises a pre-prepared medication that has been compounded at the pharmacy and disposed in the source receptacle for later use in the preparation of a dose. In this regard, the metadata for several generations of components used to prepare a medical dose order (e.g., originating from original source components received from a manufacturer such as a drug manufacturer) may be attributed to the medical dose order. As such, the medical dose order metadata may include information regarding all components used in the medical dose order including inherited metadata. The metadata for the various components may be retrieved upon identification of the receptacle 100 at the work station 40 (e.g., by way of scanning a machine readable indicium). In various embodiments, the source receptacle may include a vial, a syringe, a bottle, a bag, or other appropriate medication receptacle known in the art.

An administration receptacle may be any receptacle used during the administration of the medical dose to the patient. The administration receptacle may contain any medication, diluent, supplement, or any other material to be administered to the patient. In various embodiments, the administration receptacle may include a syringe, an IV bag, or other appropriate medication receptacle used in the administration of a substance to patient. An administration receptacle may also include metadata that is included in the metadata for the prepared medical dose order.

The transference receptacle may be used to transfer a substance from a source receptacle to the administration receptacle. For example, the transference receptacle may be a syringe or any other appropriate receptacle known in the art capable of transferring a substance from the source receptacle to the administration receptacle. A transference receptacle may also include metadata that is included in the metadata for the prepared medical dose order.

Returning to FIG. 2, the processor 70 may be in further operative communication with a display 110. In this regard, the video data stream 82 received from the imaging device 80 may be displayed on the display 110 in a manner that is perceivable by user. The video data stream 82 displayed on the display 110 may be processed by way of the video data stream processing module 72. For example, the video data stream processing module 72 may be operable to capture still images from the video data stream 82. The video data stream 82 may include a series of images displayed at a given frame rate. For example, the frame rate may be 5-10 frames/second. In another embodiment, the imaging device 80 may provide still images to the processor 70. In this regard, it may be appreciated that the discussion presented below, while described in the context of processing video data stream 82, may also be performed in the context of still digital images (e.g., on images one at a time when requested in response to a user command or the like).

The video data stream processing module 72 of the processor 70 may also be operative to capture a medical dose preparation image from the video data stream 82 received from the imaging device 80. Medical dose preparation images captured by the video data stream processing module 72 may include one or more medication receptacles 100 used in the course of preparing a medical dose order. In this regard, the preparation of medical dose orders may be documented by capturing images of the medication receptacles 100 used to prepare the dose. The medical dose preparation images may be stored as metadata regarding the medical dose order. A medical dose preparation image may include one or more medication receptacles at various stages during the preparation of the dose. For example, a source receptacle, a transference receptacle, or an administration receptacle may be imaged before, during or after preparation of the dose.

The medical dose preparation images captured by the video data stream processing module 72 may be stored in a memory 120 in operative communication with the processor 70. In this regard, the medical dose preparation images may be stored locally in the memory 120 at the work station 40. Additionally or alternatively, the medical dose preparation images may be communicated to a remote location (e.g., an on-site medication dose order database 32 or an off-site medication dose order database 34 shown in FIG. 1) by way of a network interface 140 in operative communication with the processor 70. In any regard, medical dose preparation images may be accessible such that images may be later reviewed in the course of verifying (e.g., the verifying 62 described above in relation to FIG. 1) the medical dose order and/or for maintaining records regarding the dose orders prepared by the work station 40 and/or the hospital pharmacy 12 generally.

The processor 70 may also be in operative communication with a user control device 130. The user control device 130 may be operable to receive an input from a user (e.g., a pharmacy technician preparing a dose). The user control device 130 may be, for example, a foot pedal, a button, a touch screen, a mouse, a keyboard, or other user input device known in the art. A user may utilize the user control device 130 to trigger the capture of a medical dose preparation image from the video data stream 82. For example, a medication receptacle 100 may be viewed by the user by observing the display 110 displaying the video data stream 82 captured by the imaging device 80 of imaging field 86 including the medication receptacle 100. Once the image displayed on the display 110 is acceptable to the user, the user may use the user control device 130 to trigger the capture of the medical dose preparation image for storage in the memory 120 or in a remote database as described above.

The work station 40 may also include a printer 150 that is operative to print dose labels associated with a medical product, a dose that is in progress, and/or a completed dose. In this regard, the printer 150 may be a label printer operative to print labels used in the pharmacy 12 and/or hospital in connection with metal doses and/or medical dose orders.

It may be appreciated that in the course of preparing medical dose orders in a hospital 12, the number of medical dose preparation images captured in connection with dose orders may be extremely large. For example, a plurality of images may be captured in connection with each dose prepared. For most hospitals, the number of doses prepared daily may be on the order of hundreds of doses or more. In this regard, the memory resources necessary to store images captured in connection with the preparation of medical dose orders may be large, especially considering the practice of hospitals of storing archived images for dose orders.

Furthermore, because medical dose preparation images may be used by a pharmacist to verify medical dose orders prior to dispensing orders from the pharmacy, image resolution may be at a premium in order to facilitate accurate review by the pharmacist of images. Accordingly, the need for large memory resources dedicated to storing medical dose preparation images is exacerbated. Accordingly, any reduction in image size (e.g., as represented by the size of the image in memory) may be advantageous to reduce the memory resources required for storage of images and/or to allow more efficient use of memory resources available for the storage of medical dose preparation images.

As such, capturing medical dose preparation images including the entire imaging field 86 may be an inefficient use of memory resources. Cropping images to retain relevant portions of the imaging field 86 (i.e., those containing medication receptacles 100) for storage may be a more efficient use of memory resources than storing an image of the entire imaging field 86. For example, for a given resolution, the overall image dimensions may be reduced to reduce the size in memory of the image. Additionally or alternatively, for an image with reduced overall dimensions, the image resolution may be increased without an increase in the size of the image in memory compared to an image of the entire imaging field 84 at a reduced resolution.

However, requiring an operator to manually crop each image of the imaging field 86 may add time to the preparation of medical dose orders. This may result in increased costs associated with preparation of medical disorders or be undesirable based on scheduling requirements for doses, especially "stat" doses that may be critical to the life of a patient. In this regard, the video data stream processing module 72 may be operative to perform an auto cropping operation on the video data stream 82 acquired by the imaging device 80 so as to identify relevant portions of the video data stream 82 for storage to reduce the memory resources needed to store medical dose preparation images while not impacting the speed of the preparation of medical dose orders.

Figure 3:
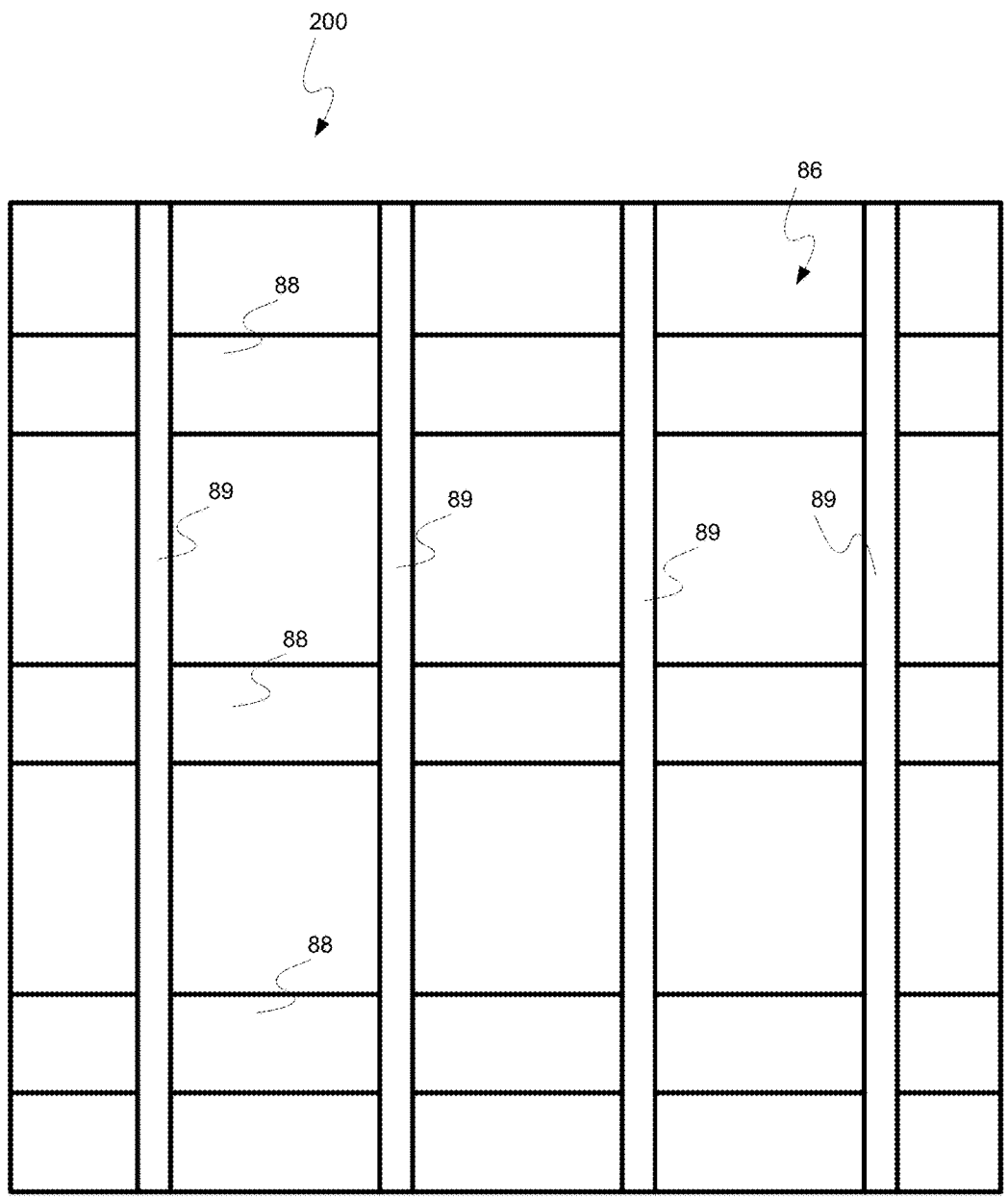
FIG. 3 depicts an embodiment of a background image for use in an embodiment of an auto cropping operation.

In an embodiment, an auto cropping operation may involve comparing the video data stream 82 with a background image to identify a region of interest corresponding to an object disposed in the imaging field in the video data stream 82. With further reference to FIG. 3, an example of a still image representing one instance in time of the video data stream 82 acquired by the imaging device 80 of the medical dose preparation staging region 86 is depicted. The medical dose preparation staging region 86 may include medication receptacle engagement features such as grooves 88, channels 89, or other features adapted to engage medication receptacles 100 to retain medication receptacles 100 stationary in the medical dose preparation staging region 86. In FIG. 3, no medication receptacles 100 are present such that the medical dose preparation staging region 86 is devoid of any objects. This image may be captured as a background image 200 that depicts the appearance of the medical dose preparation region 86 in video data stream 82 when no medication receptacles 100 are present. Of note, the base 90 may extend across the entire imaging field 84 to occupy substantially all of the background in the image field 84. The background image 200 may be compared during the auto cropping operation to a video data stream 82 from the imaging device 80. The background image may be stored remotely or locally (e.g., in the memory 120 of the work station in a background image store 124).

In an embodiment, a plurality of background images 200 may be obtained such that different ones of the plurality of background images 200 are employed in the auto cropping operation depending upon the location and/or orientation of the imaging device 80. For example, the imaging device 80 may be positionable in a plurality of positions. Accordingly, depending upon the position of the imaging device 80, the background image 200 may differ. In this regard, a sensor may be provided to determine the position in which the imaging device 80 disposed such an appropriate corresponding one of the plurality of background images may be used based on the identified position of the imaging device 80.

Figure 4:
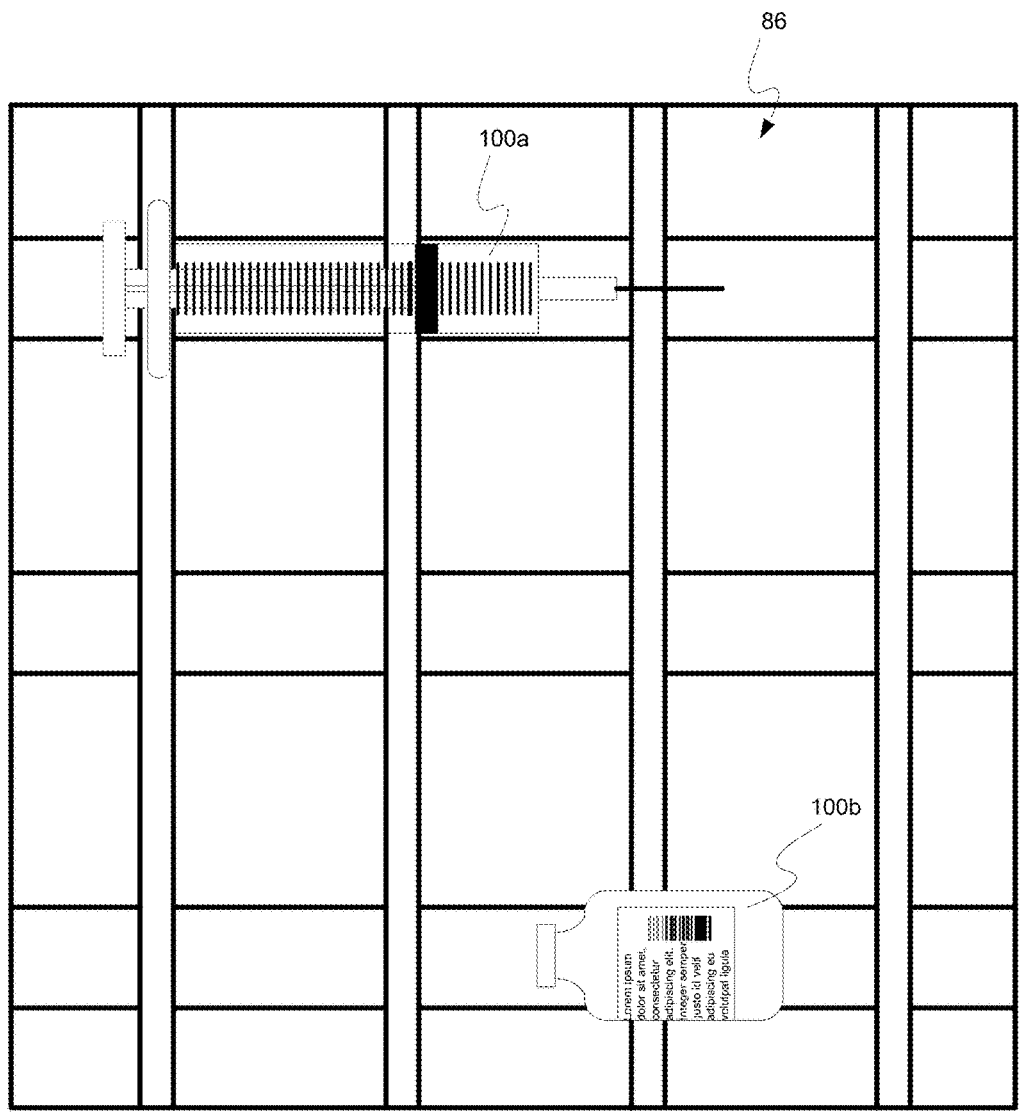
FIG. 4 depicts an embodiment of a video data stream that may be the subject of an auto cropping operation.

In any regard, after a background image 200 has been attained, one or more medication receptacles 100 may be disposed in the medical dose preparation staging region 86 as depicted in FIG. 4. For example, as shown in FIG. 4, a syringe 100*a* and a vial 100*b* have been disposed in the medical dose preparation staging region 86. As can be appreciated, the medication receptacle engagement features (88, 89) may at least generally correspond to the medication receptacles 100 disposed in the medical dose preparation staging region 86. In any regard, the video data stream 82 obtained from the imaging device 80 may now include the medication receptacles 100a and 100b as shown in FIG. 4. The auto cropping operation may generally include comparing the background image 200 obtained of the medical dose preparation staging region 86 without medication receptacles 100 disposed thereon to the video data stream 82 including medication receptacles 100 having been disposed in the medical dose preparation staging region 86 to determining regions of interest corresponding to the medication receptacles 100.

In this regard, upon analysis of the differences between the background image 200 and video data stream 82, a plurality of locations representing differences between the video data stream 82 and the background image 200 corresponding to the medication receptacles 100 may be determined such that regions of interest encompassing the medication receptacles 100 may be determined. In turn, the medical dose preparation images captured may contain image data corresponding only to the regions of interest identified including the medication receptacles 100 and may exclude a portion or all of the imaging field 86 outside the region of interest.

In an embodiment, a subset (e.g., a predetermined subset) of the video data stream 82 may be compared to a corresponding subset of the background image 200 to identify differences between the video data stream 82 and the background image 200 corresponding to the presence of medication receptacles 100. By comparing only a subset of the video data stream 82 against a corresponding subset of the background image 200, the amount of data to be processed may be reduced such that the auto cropping operation may occur more quickly to prevent the slowing of the preparation of medical doses.

In this regard, the auto cropping operation described herein may occur substantially faster than a method where every pixel of an image is analyzed to determine differences between a video data stream 82 and a background image 200. As such, the auto crop operation described herein may provide an accurate automatic crop operation with a very fast execution time. For example, the auto crop operation described herein may occur for a given frame of the video data stream 82 prior to obtaining the next frame in the video data stream 82. For example, in the embodiment where the imaging device 80 to collects video at 5-10 frames per second, the auto cropping operation may be completed faster than the frame rate of the imaging device 80 (i.e., at least within 100 ms for a frame rate of 10 frames/second). That is, the auto cropping algorithm may execute in a time less than the refresh rate of the video data stream. In this regard, the auto cropping operation may identify a region of interest for each image in the video data stream 82 prior to obtaining the next image in the video data stream 82.

Figure 5:
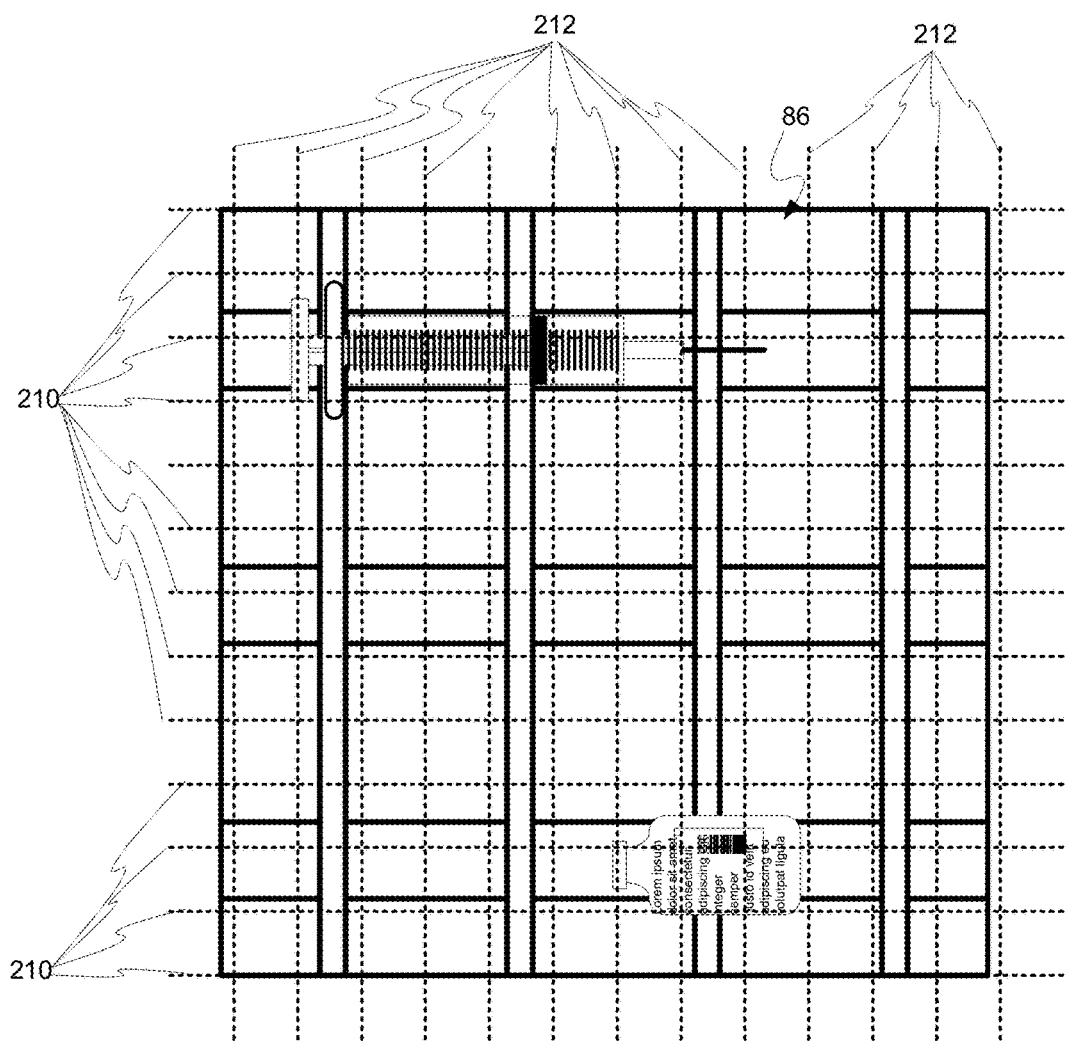
FIG. 5 depicts the video data stream of FIG. 4 with a subset of the image identified.

With reference to FIG. 5, an embodiment of a potential subset of the video data stream 82 is shown that may correspond to selected pixels of the video data stream 82. For example, the pixels comprising the subset of the video data stream 82 may be taken along a plurality of horizontal grid lines 210 and a plurality of vertical grid lines 212 as depicted in FIG. 5. As such, the horizontal grid lines 210 may extend in a first direction corresponding to the width of the medical dose preparation staging region 86. For example, the horizontal grid lines 210 may extend across substantially the entire width of the medical dose preparation staging region 86 and/or the entire width of the imaging field 86. The vertical grid lines 212 may extend in a second direction corresponding to the length of the medical dose preparation staging region 86. For example, the vertical grid lines 212 may extend across substantially the entire length of the medical dose preparation staging region 86 and/or the entire length of the imaging field 86.

Figure 6:
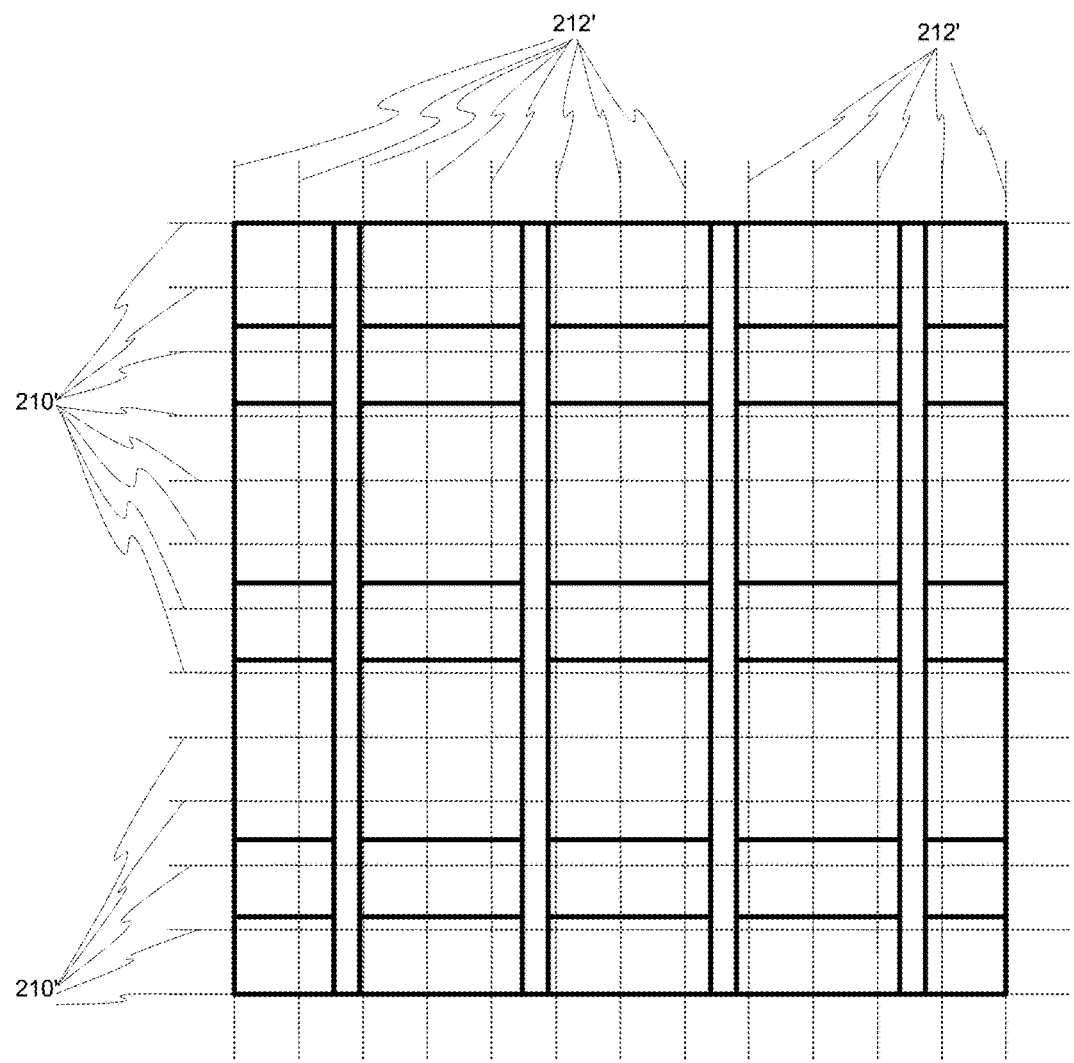
FIG. 6 depicts the background image of FIG. 3 with a subset of the background image corresponding to the subset of FIG. 5 identified.

The grid lines 210 and 212 may extend in at least two directions over the imaging field such that the length and the width of a region of interest may be determined relative to the grid lines 210 and 212. With further reference FIG. 6, a corresponding predetermined subset of pixels taken along grid lines 210' and 212' in the background image 200 corresponding to grid lines 210 and 212 shown in FIG. 5 may be used in the comparison.

The grid spacing of the predetermined portion of the video data stream 82 and the background image 200 may be selected based on the smallest object anticipated to be imaged. For example, the spacing of the grid lines 210, 212 may be selected such that the least two grid lines 210, 212 cross any medication receptacle 100 that may be placed in the medical dose preparation staging region 86 such that the extent of the bounding area may be accurately determined for each medication receptacle 100.

Figure 7:
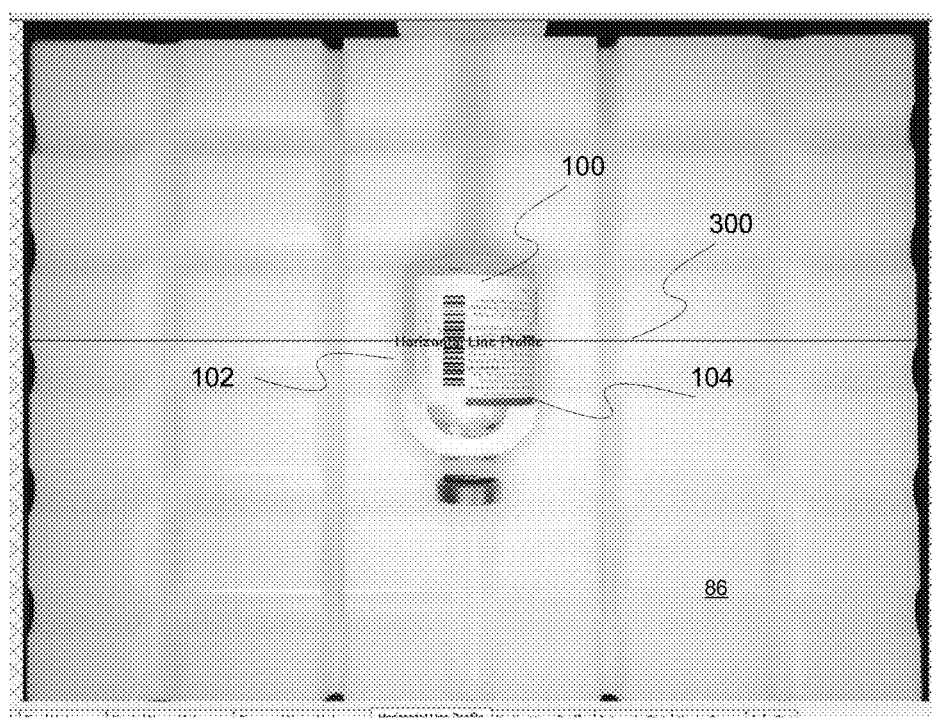
FIG. 7 depicts an embodiment of an image taken from a video data stream.

With additional reference to FIGS. 7-10, the data compared during the auto cropping operation may correspond to data extracted from each pixel along each gridline of the video data stream and the background image. For example, FIG. 7 shows a medication receptacle 100 that has been disposed in the imaging field 86. For purposes of illustration, a single horizontal line 300 is shown which intersects the lateral edges 102 and 104 of the medication receptacle 100.

The video data stream processing module 72 may extract color bitmap data along the horizontal line 300. The video data stream processing module 72 may convert the data for each pixel taken along the horizontal line 300 into an array of grayscale data corresponding to intensity data for each pixel. In one embodiment, the video data stream processing module 72 may convert grayscale data for each pixel into a quantitative value representing the relative color of the grayscale data for each pixel between white and black. For example, an 8 bit value may be established on a scale of 0-255 where zero represents black and 255 represents white for a pixel. Accordingly, the intensity data for each pixel may correspond to a value representative of the pixels location in the grayscale between white and black.

Figure 8:
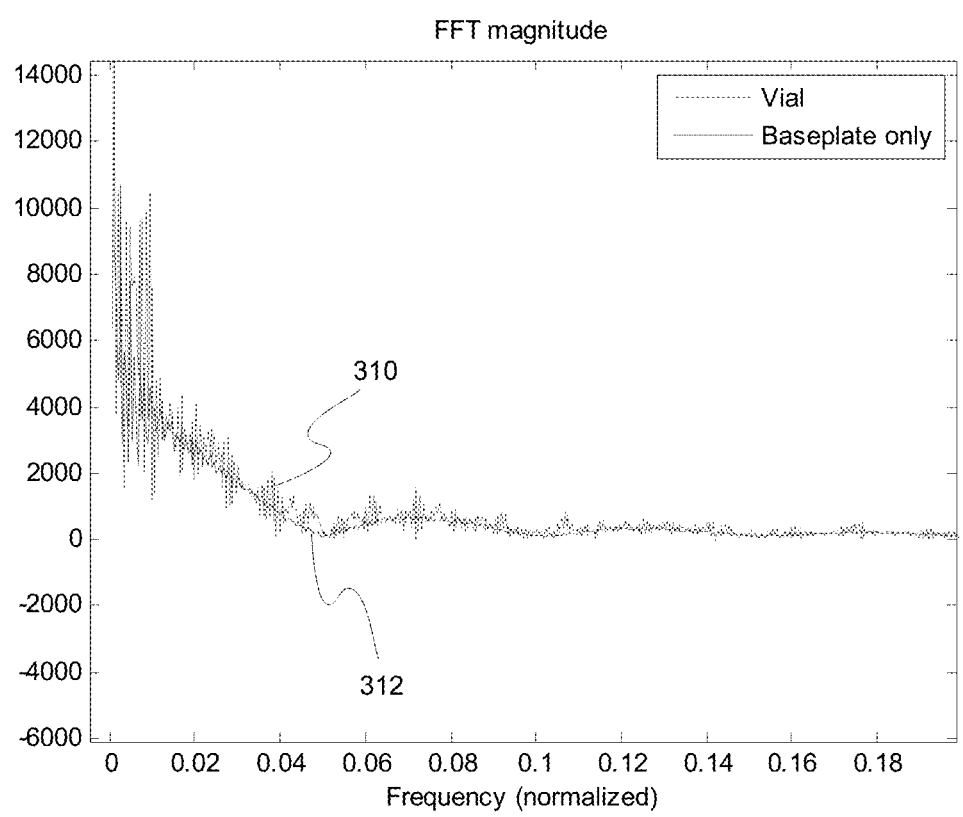
FIG. 8 is a plot depicting a mathematical transform of data obtained from the image of FIG. 7.

Various processing techniques may be applied to the intensity data of the pixels taken along the horizontal line. For example, a transform of the data into the frequency domain using a mathematical transform (e.g., fast Fourier transform (FFT)) may be applied to the intensity data. FIG. 8 depicts the results one example of an FFT of data taken along the horizontal line 300 from FIG. 7. A first line 310 corresponds to data from the video data stream 82 depicted in FIG. 7 including the medication receptacle 100 and a second line 312 corresponds to data from a corresponding horizontal line in a background image of the imaging field of FIG. 7 without the medication receptacle 100.

As can be appreciated from FIG. 8, significant low-frequency content up until about 5% full frequency is present. Any deviation of the first line 310 from the second line 312 in the higher frequencies may result from effects of the FFT process and may not be real. Accordingly, a high pass cutoff frequency may be established to effectively eliminate low-frequency intensity changes. The threshold for high pass filter may be selected considering that too low a high pass filter threshold may eliminate robustness against lighting changes, which will mostly show up as low-frequency data in the FFT plot.

Figure 9:
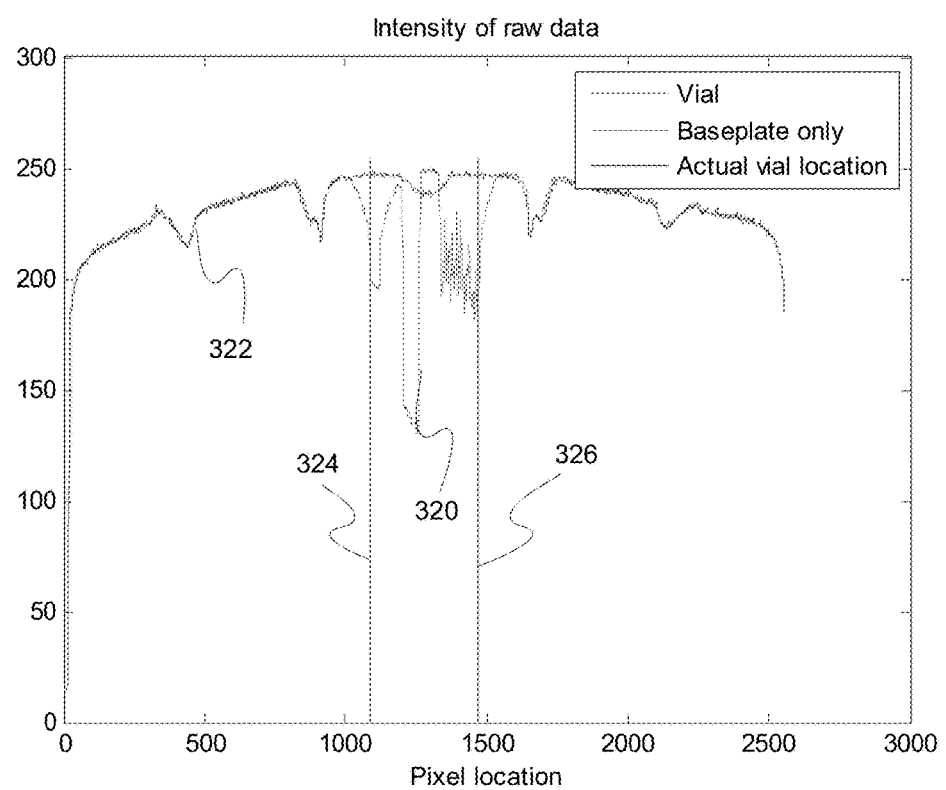
FIG. 9 is a plot depicting raw pixel intensity data obtained from the image of FIG. 7.

With further reference to FIG. 9, the raw intensity data for pixels taken along the horizontal line 300 of the video data stream shown in FIG. 7 is plotted using plot line 320 and raw intensity data for pixels taken along a corresponding horizontal line of a background image is plotted using plot line 322. The vertical axis of the plot in FIG. 9 represents intensity data (e.g., quantified grayscale data as described above) and the horizontal axis represents pixel location along the horizontal line of FIG. 7. Vertical lines 324 and 326 in FIG. 9 represent the location in the plot of FIG. 9 of the lateral edges 102 and 104, respectively, of the medication receptacle 100 shown in FIG. 7. As may be appreciated, the deviation between the video data stream plot line 320 and the background image plot line 322 may not include sharp edges such that the location of the edges 102, 104 of the medication receptacle 100 may be difficult to detect using the raw intensity data.

Figure 10:
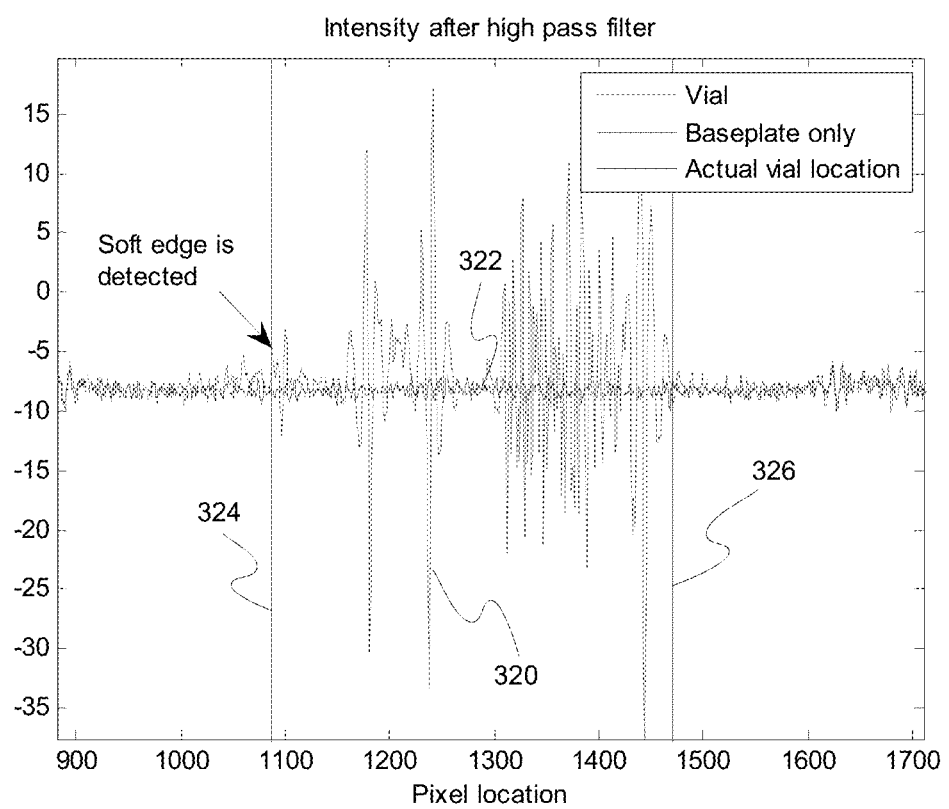
FIG. 10 is a plot depicting processed intensity data from the image of FIG. 7.

However, FIG. 10 (whose axes also represent deviation in intensity along the vertical axis and pixel location on the horizontal axis) depicts a similar plot having undergone high pass filtering. As may be appreciated, the deviations at the left edge 102 (represented by vertical line 324) and at the right edge 104 (represented by vertical line 326) of the medication receptacle 100 are more pronounced such that the edge 102, 104 of the medication receptacle 100 may be detected. Note that this is even the case on the left lateral edge 102 of the medication receptacle 100 were no label is present at the edge 102 in the video data image of FIG. 7. In this regard, the left edge 102 represents a "soft edge." The term "soft edge" is intended to denote a situation where an edge of the medication receptacle 100 does not have a label portion present at the edge as is shown on the left side 102 of the medication receptacle 100 in FIG. 7. That is, a soft edge may correspond to a completely translucent or transparent edge portion of the medication receptacle 100. It may be appreciated such soft edges may present less pronounced differences between the video data stream data in the background image data as can be appreciated in comparing the deviations on the left side (324) and right side (326) of the plot in FIG. 10, respectfully. However, upon inspection of the filter data in FIG. 10, the edges of the medication receptacle 100 are clearly denoted and may be identified.

Furthermore, processing may be performed on the intensity data for each pixel to assist in improving the accuracy of the auto cropping operation. For example, the intensity data may be filtered using any number of additional or alternative filtering techniques known the art.

Additionally, the rate of change of the intensity along each grid line 210, 212 rather than raw intensity data for each pixel may provide a more accurate measure of the presence or absence of a medication receptacle 100 disposed in a medical dose preparation staging region 86. In this regard, the derivative of the raw intensity data 320 may be calculated to reflect the rate of change of intensity along each grid line 210, 212 to assist in determining the location of an edge of a medication receptacle 100 disposed in the medical dose preparation staging region 86.

Furthermore, during the correlation of the subset of the video data stream 82 with the background image 200, each pixel of the video data stream 82 may be compared to a directly corresponding pixel in the background image 200 or each pixel of the video data stream 82 may be compared to a plurality of pixels within a certain predetermined distance along the corresponding grid line in the background image 200 of a directly corresponding pixel. For example, any given pixel for the video data stream 82 may be compared to pixels within about +/−10 pixels of the directly corresponding pixel in the background image 200. Thus, slight variations between the position of the background image 200 relative to the video data stream 82 and/or minor lighting variations may be accommodated that may otherwise be attributed to identified edges of medication receptacles 100. For example, the video data stream 82 corresponding to the background image 200 may move slightly and/or be subject to slightly different lighting such that minor variations may occur. However, by comparing a given pixel in the video data stream 82 with a range of pixels in the corresponding background image 200, and minor variations may be accounted for.

Figure 11:
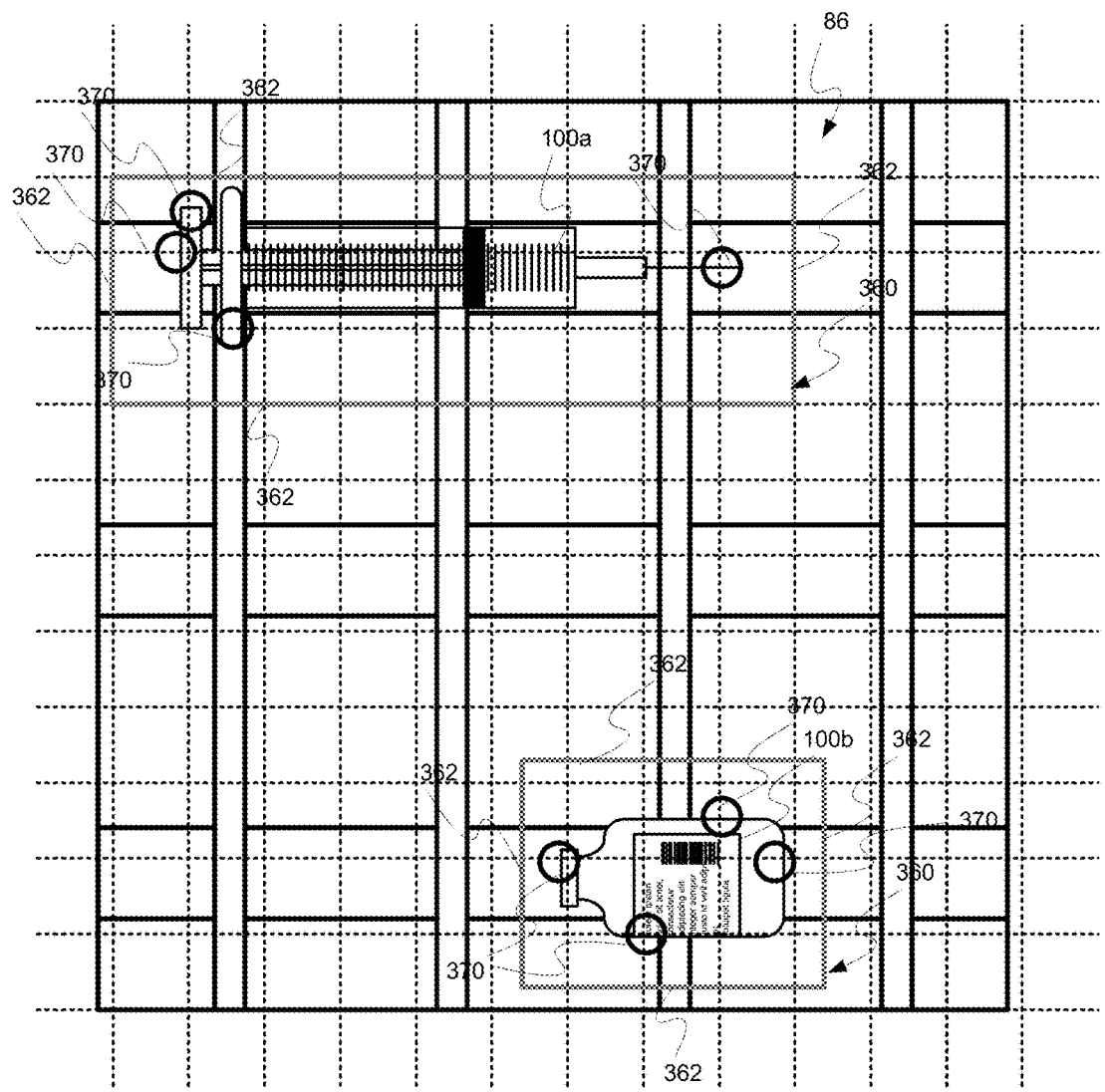
FIG. 11 depicts the video data stream of FIG. 4 with certain features applicable to the auto cropping operation highlighted.

Based on the analysis of the video data stream 82 in relation to the background image 200, the edges of a given medication receptacle 100 may be determined along each grid line 210, 212. For example, a difference identified along a grid line 210, 212 that exceeds a predetermined rate of change may be attributed to a location 370 of an edge of a medication receptacle 100. Based on the locations 370 at each grid line 210, 212 corresponding to determined edges of medication receptacles 100, a bounding area 360 (e.g., as shown in FIG. 11). The bounding area 360 may be comprised of edges 362 that may be located in correspondence to identified locations 370 of the edges of a medication receptacle 100 in the video data stream 82. For example, the minimum and maximum location 370 determined along each of the horizontal grid lines 210 hits may be used to determine a horizontal position of the edges 362 of the bounding area 360. In an implementation, the minimum and maximum location 370 determined along each vertical grid line 212 may be used to determine the vertical position of the edges 362 of the bounding area 362. Furthermore, in an embodiment, the edges 362 of the bounding area 360 may be extended beyond the minimum and maximum locations 370 in both the vertical and horizontal direction to the next grid line beyond the minimum and maximum location 370. For example, a medication receptacle 100 may extend beyond a grid line 210 or 212 such that a location 370 is identified. While the medication receptacle 100 may extend beyond a grid line 210 or 212, the receptacle 100 may not extend to the next adjacent grid line. Thus, if the bounding area 360 were to be established at the location 370, a portion of the medication receptacle 100 may not be included within the bounding area 360. As such, the bounding area 360 may be automatically expanded to include the area up to the next adjacent grid line in both the horizontal and vertical directions beyond the minimum and maximum identified location 370 for a given medication receptacle 100.

With further reference to FIG. 11, by comparing the background image 200 to a video data stream 82 along the predetermined subset of the video data stream 82 and background image 200, locations 370 corresponding to differences between the background image 200 and video data stream may be located in the manner described above. In turn, locations 370 along the grid lines 210 and 212 may be identified as indicated in FIG. 11 that correspond to the minimum and maximum locations of differences between the video data stream 82 and the background image 200 along both the horizontal and vertical grid lines 210 and 212. Based on these locations 370, edges 362 of a bounding area 360 may be established around each medication receptacle 100.

As may further be appreciated in FIG. 11, more than one medication receptacle 100 may be disposed in the imaging field 86 at any one time. The video stream data processing module 72 may be operative to separately identify the plurality of medication receptacles 100 such that discrete bounding areas 360 are established for each medication receptacle 100 individually. While two medication receptacles 100 are depicted in FIG. 11, it may be appreciated that additional or fewer medication receptacles 100 may be identified such that additional or fewer corresponding bounding areas 360 are established by the video data stream processing module 72 of the processor 70.

In this regard, the auto cropping operation may include logic to individually identify different medication receptacles 100 disposed in imaging field 86. For example, logic may be employed wherein if a certain predetermined distance along a grid line 210, 212 does not have any differences compared to the background image 200, the locations 370 at the extends of a distance exceeding the predetermined distance may be attributed to separate medication receptacles 100. Additionally or alternatively, an analysis may be performed to identify a perimeter of a medication receptacle 100 such that individual medical receptacles 100 may be identified based on identification of a unitary closed perimeter. For example, for a given close perimeter, the auto cropping operation may determine a single medication receptacle 100 exists and dedicate a single bounding box to the identified medical receptacle 100.

Figure 12:
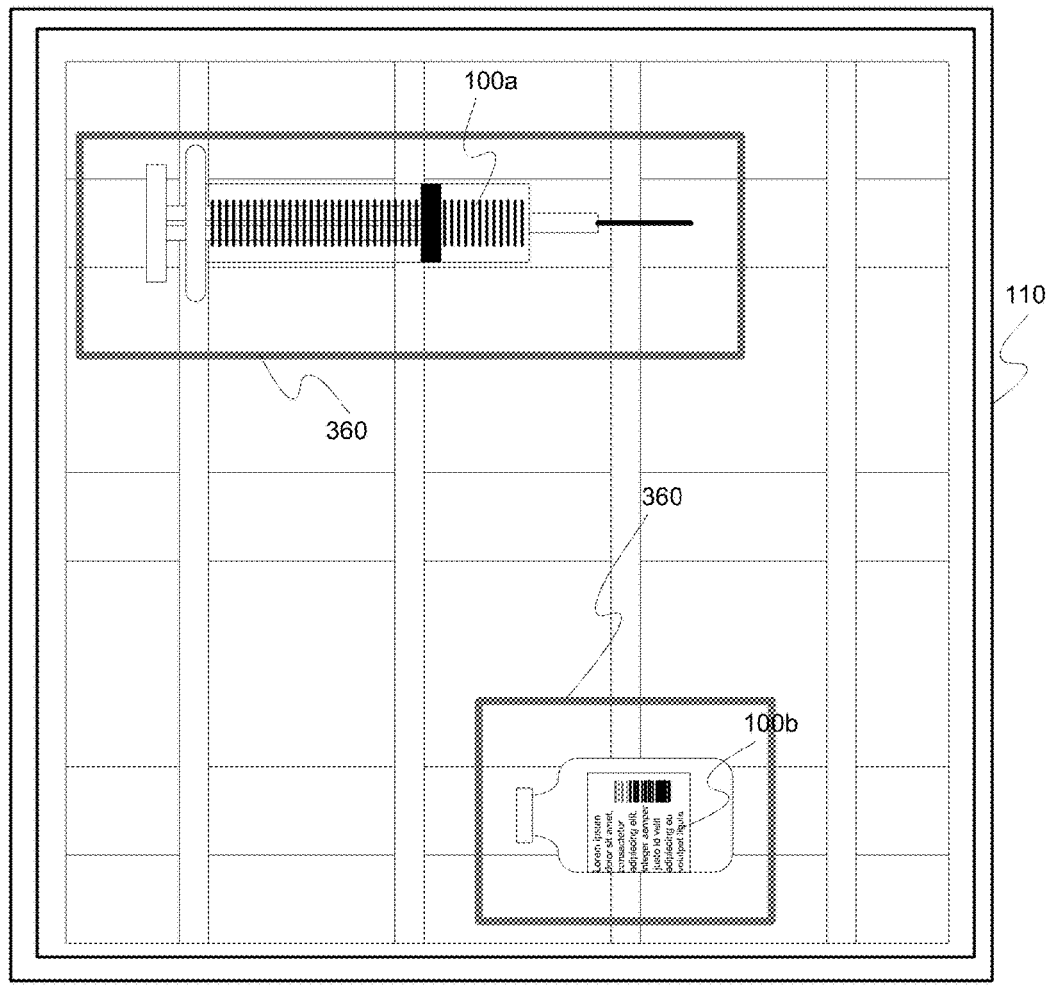
FIG. 12 depicts a display output perceivable by a user corresponding to the video data stream of FIG. 4 once an auto cropping operation has been performed thereon.

With further reference FIG. 12, an example of the output of the display 110 is shown. It may be appreciated that the grid lines 210 and 212 corresponding to the subset of the video data stream 82 analyzed to determine the bounding areas 360 may not be shown on the display 110. However, the bounding areas 360 may be represented on the display 110 such that the region of interest identified by the video data stream processing module 72 may be perceivable by a user viewing the display 110. In this regard, once the bounding area 360 has been established for each of the medication receptacles 100, the display 110 may be configured to display the bounding area 360 in relation to the video data stream 82 on the display 110 such that the user may verify that the bounding area 360 includes all relevant portions of the medication receptacle 100 in the bounding area 360.

The user may have the opportunity to expand or contract the bounding area 360 displayed to increase or decrease the size of the region of interest surrounding a medication receptacle 100 in the video data stream 82. In an embodiment, if the bounding box 320 is incorrectly determined by the auto cropping operation the user may employ a marker or other object disposed in the medical dose preparation staging area 86 that provides a high contrast to the background 200 to establish an edge location 370 for a bounding area 360. For example, an object may be disposed adjacent to the medication receptacle 100 to positively establish an edge 362 of the bounding area 360 beyond the extent of the medication receptacle 100. The object may be a discrete object such as a marker or the like that is placed in the imaging field 86, or the user may employ his or her finger or other pointing device disposed in imaging field 86 to positively establish a location 370.

Figure 13:
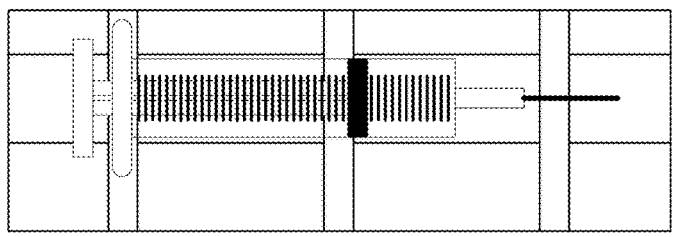
FIGS. 13 and 14 are examples of medical dose preparation images obtained from the video data stream of FIG. 4 resulting from an auto cropping operation performed thereon.
Figure 14:
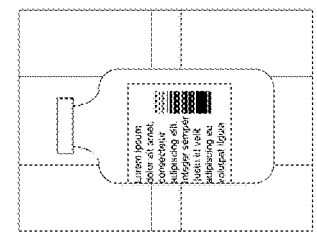

Once the region of interest has been established by the user, the user may utilize the user control device 130 to initiate the capture of medical dose preparation images corresponding to the portion of the video data stream 82 included in the bounding box 320 (i.e., the region of interest). For example, FIGS. 13 and 14 depict the medical dose preparation images corresponding to the two medication receptacles 100a and 100b, respectively, contained in the video data stream 82 depicted on the display 110 shown in FIG. 12 that may be captured upon the user utilizing the user control device 130 to initiate capture of the images when the bounding areas 360 are establish as shown in FIG. 12.

In an embodiment, the bounding area 360 may be represented a box superimposed over the video data stream 82 in a manner perceivable by the user. Additionally or alternatively, the area outside the bounding area 360 not to be included in the medical dose preparation image may be displayed in a manner different than the area within the bounding area 360 to be included in the medical dose preparation image. For example, the area of the imaging field 86 outside a bounding area 360 may be displayed as a dimmed or shadowed image that clearly identifies to the user that the area outside the bounding areas 360 is to be not included in the medical dose preparation image.

While the invention has been illustrated and described in detail in the drawings and foregoing description, such illustration and description is to be considered as exemplary and not restrictive in character. For example, certain embodiments described hereinabove may be combinable with other described embodiments and/or arranged in other ways (e.g., process elements may be performed in other sequences). Accordingly, it should be understood that only the preferred embodiment and variants thereof have been shown and described and that all changes and modifications that come within the spirit of the invention are desired to be protected.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain known modes of practicing the invention and to enable others skilled in the art to utilize the invention in such or other embodiments and with various modifications required by the particular application(s) or use(s) of the present invention. It is intended that the appended claims be construed to include alternative embodiments to the extent permitted by the prior art.

What is claimed is:

1. A work station for use in a system for medical dose preparation management, the work station comprising:
   a stand including:
      an imaging device having an imaging field encompassing a medical dose preparation staging region, the imaging device being operable to output digital image data of the imaging field including the medical dose preparation staging region;
      a base having a support surface; and
      a support extending away from the base to support the imaging device relative to the base;
   a processor in operative communication with the imaging device to receive the digital image data of the imaging field;
   a display in operative communication with the processor to receive the digital image data of the imaging field and display a corresponding image of the imaging field that is perceivable by a user, wherein the processor is operable to process the digital image data to identify at least one region of interest within the imaging field corresponding to at least one medication receptacle disposed on the support surface of the base in the medical dose preparation staging region, wherein the region of interest is visually differentiated in relation to said corresponding image on the display by the processor in a manner perceivable by the user;

a user control device in operative communication with the processor to initiate the capture of medical dose preparation image data from the digital image data at the processor, wherein the medical dose preparation image data includes image data corresponding to at least a portion of the region of interest that is visually differentiated in relation to said corresponding image on the display, and that excludes other image data corresponding with another portion of the imaging field; and a memory in operative communication with the processor to receive and store the medical dose preparation image data.

2. The work station according to claim 1, further comprising: a printer to print labels in association with fulfillment of medical dose orders.

3. The work station according to claim 1, said user control device comprising one of the following:
a foot pedal;
a button;
a touch screen;
a mouse; and,
a keyboard.

4. The work station according to claim 1, wherein the digital image data comprises a video data stream, and wherein the processor is operable to analyze a predetermined subset of the digital image data of the video data stream to identify the region of interest.

5. The work station according to claim 1, wherein the processor is operable to analyze a predetermined subset of the digital image data to identify the region of interest.

6. The work station according to claim 5, wherein the analysis includes comparing the predetermined subset of the digital image data to a corresponding subset of a background image of the medical dose preparation staging region that does not include any medication receptacle in the medical dose preparation staging region.

7. The work station according to claim 6, wherein the imaging device is positionable in a plurality of different positions, and wherein said background image is a corresponding one of a plurality of different background images corresponding with the plurality of different positions.

8. The work station according to claim 6, wherein the predetermined subset of the digital image data corresponds to a plurality of pixels of the digital image data that extend across the digital image data in at least a first direction.

9. The work station according to claim 8, wherein the plurality of pixels extend across the digital image data in a second direction perpendicular to the first direction.

10. The work station according to claim 9, wherein the plurality of pixels form a grid over the digital image data, and wherein the grid comprises grid lines that are spaced in relation to a known size of medication receptacles.

11. The work station according to claim 10, wherein the at least one region of interest is defined by a bounding area on the display.

12. The work station according to claim 11, wherein said bounding area is defined by a plurality of edges that are each disposed at an identified location of the predetermined subset of the digital image data at least partially based on a threshold difference between the digital image data and the background image at the identified location.

13. The work station according to claim 12, wherein the processor is operable to calculate intensity data for each pixel of the predetermined subset of the digital image data and for each pixel of the corresponding predetermined subset of the background image.

14. The work station according to claim 13, wherein said intensity data is processed utilizing frequency domain processing.

15. The work station according to claim 13, wherein said intensity data undergoes at least one of high pass filtering and low pass filtering.

16. The work station according to claim 12, wherein the threshold difference comprises a predetermined difference in intensity data between the predetermined subset of the digital image data and the corresponding subset of the background image.

17. The work station according to claim 12, wherein each pixel of the predetermined subset of the digital image data is compared to a plurality of adjacent corresponding pixels from the corresponding subset of the background image.

18. The work station according to claim 12, wherein the identified location corresponds to one of a minimum or maximum threshold difference along the grid lines in the first direction or in the second direction.

19. The work station according to claim 12, wherein the identified location is selected to correspond to the next most remote grid line of the grid exterior to the threshold difference in the first direction and in the second direction along the grid line.

20. The work station according to claim 11, wherein the bounding area is represented by at least one of a superimposed box, and has an area displayed in a manner different than that of an area outside of the bounding area.

* * * * *